United States Patent [19]

Vacca et al.

[11] Patent Number: 5,717,097
[45] Date of Patent: Feb. 10, 1998

[54] HIV PROTEASE INHIBITORS USEFUL FOR THE TREATMENT OF AIDS

[75] Inventors: Joseph P. Vacca, Telford; Bruce D. Dorsey, Harleysville; James P. Guare, Quakertown; M. Katharine Holloway; Randall W. Hungate, both of Lansdale; Rhonda B. Levin, Lafayette Hill; Joel R. Huff, Gwynedd Valley, all of Pa.

[73] Assignee: Merck & Co., Inc., Rahway, N.J.

[21] Appl. No.: 759,203

[22] Filed: Dec. 4, 1996

Related U.S. Application Data

[63] Continuation of Ser. No. 533,142, Sep. 25, 1995, abandoned, which is a continuation of Ser. No. 235,576, Apr. 29, 1994, abandoned, which is a continuation-in-part of Ser. No. 59,038, May 7, 1993, Pat. No. 5,413,999, which is a continuation-in-part of Ser. No. 40,729, Mar. 31, 1993, abandoned, which is a continuation-in-part of Ser. No. 883,825, May 15, 1992, abandoned, which is a continuation-in-part of Ser. No. 789,508, Nov. 8, 1991, abandoned.

[51] Int. Cl.[6] ............... C07D 241/04; C07D 401/06
[52] U.S. Cl. .......................... 544/360; 544/390
[58] Field of Search ............................. 544/360, 390

[56] References Cited

U.S. PATENT DOCUMENTS 5,413,999  5/1995  Vacca et al. ............... 544/360

Primary Examiner—Joseph McKane
Attorney, Agent, or Firm—Mary A. Appollina; Melvin Winokur

[57] ABSTRACT

Compounds of formula

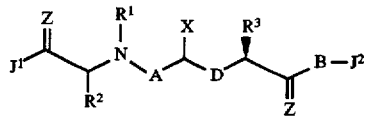

where A is usually carbonyl or —$CH_2$—, D is usually —$CH_2$—; $R^1$ and $R^2$ are independently hydrogen or optionally-substituted $C_{1-4}$alkyl or aryl, or $R^1$ and $R^2$ are joined together to form a monocyclic or bicyclic ring system, are HIV protease inhibitors. These compounds are useful in the prevention or treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

6 Claims, No Drawings

HIV PROTEASE INHIBITORS USEFUL FOR THE TREATMENT OF AIDS

This application is a continuation of application Ser. No. 08/533,142, filed Sep. 25, 1995, now abandoned which is a continuation of Ser. No. 08/235,576, filed Apr. 29, 1994, now abandoned, which is a continuation-in-part of Ser. No. 08/059,038, filed May 7, 1993, now issued as U.S. Pat. No. 5,413,999, which is a continuation-in-part of Ser. No. 08/040,729, filed Mar. 31, 1993, now abandoned, which is a continuation-in-part of Ser. No. 07/883,825, filed May 15, 1992, now abandoned, which is a continuation-in-part of Ser. No. 07/789,508, filed Nov. 8, 1991, now abandoned; the contents of all previous applications are hereby incorporated by reference.

The present invention is concerned with compounds which inhibit the protease encoded by human immunodeficiency virus (HIV) or pharmaceutically acceptable salts thereof and are of value in the prevention of infection by HIV, the treatment of infection by HIV and the treatment of the resulting acquired immune deficiency syndrome (AIDS). It also relates to pharmaceutical compositions containing the compounds and to a method of use of the present compounds and other agents for the treatment of AIDS and viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad., Sci.*, 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313, 277(1985)]. Amino acid sequence homology provides evidence that the pol sequence encodes reverse transcriptase, an endonuclease and an HIV protease [Toh, H. et al. *EMBO J.*, 4, 1267 (1985); Power, M. D. et al., *Science*, 231, 1567 (1986); Pearl, L. H. et al., *Nature*, 329, 351 (1987)]. Applicants demonstrate that the compounds of this invention are inhibitors of HIV protease.

BRIEF DESCRIPTION OF THE INVENTION

Compounds of Formula I, as herein defined, are disclosed. These compounds are useful in the inhibition of HIV protease, the prevention of infection by HIV, the treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS, methods of preventing infection by HIV, and methods of treating infection by HIV are also disclosed.

Some abbreviations that may appear in this application are as follows.

ABBREVIATIONS

| Designation | |
|---|---|
| | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| | Activating Group |
| HBT (HOBT or HOBt) | 1-hydroxybenzotriazole hydrate |
| | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloride |
| EDC | 1-ethyl-3-(3-dimethylaminopropyl)carbodiimide hydrochloride |
| | Other |
| (BOC)₂O (BOC₂O) | di-t-butyl dicarbonate |
| n-Bu₄N⁺F⁻ | tetrabutyl ammonium fluoride |
| nBuLi (n-Buli) | n-butyllithium |
| DMF | dimethylformamide |
| Et₃N | triethylamine |
| EtOAc | ethyl acetate |
| TFA | trifluoroacetic acid |
| DMAP | dimethylaminopyridine |
| DME | dimethoxyethane |
| LDA | lithium diisopropylamide |
| THF | tetrahydrofuran |
| | Amino Acid |
| Ile | L-isoleucine |
| Val | L-valine |

DETAILED DESCRIPTION OF THE INVENTION AND PREFERRED EMBODIMENTS

This invention is concerned with compounds of Formula I, combinations thereof, or pharmaceutically acceptable salts thereof, in the inhibition of HIV protease, the prevention or treatment of infection by HIV and in the treatment of the resulting acquired immune deficiency syndrome (AIDS). Compounds of Formula I are defined as follows:

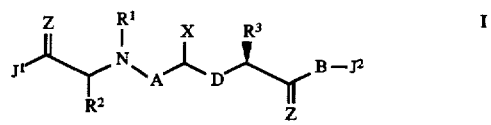

wherein:

A is

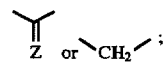

X is independently —OH, —NH₂, F, or =O;
Z is independently =O, =S, or =NH;
D is —(CR$^a$₂)—;
wherein:
R$^a$ is each independent of the other,
1) —H,
2) —OH,
3) —NH₂, 4) —F,
5) —C$_{1-4}$alkoxy,
6) —SH,
7) -arylthio-, or
8) C$_{1-4}$alkyl;

R is hydrogen or C$_{1-4}$ alkyl;

R$^1$ and R$^2$ are independently:
1) hydrogen,
2) —C$_{1-4}$ alkyl unsubstituted or substituted with one or more of
   a) halo,
   b) hydroxy,
   c) C$_{1-3}$ alkoxy,
   d) aryl unsubstituted or substituted with one or more of C$_{1-4}$alkyl, amino, hydroxy or aryl,
   e) —W-aryl or —W-benzyl, wherein W is —O—, —S—, or —NH—,
   f) a 5-7 membered cycloalkyl group unsubstituted or substituted with one or more of
      i) halo,
      ii) hydroxy,
      iii) C$_{1-3}$ alkoxy, or
      iv) aryl,
   g) heterocycle unsubstituted or substituted with one or more of hydroxy, oxo, halo, C$_{1-4}$ alkoxy, C$_{1-4}$alkyl optionally substituted with hydroxy;

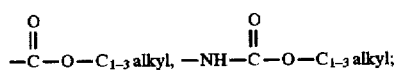

or Boc, h)

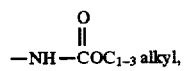

i)

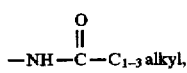

j) —NH—SO$_2$C$_{1-3}$alkyl,
k) —NR$_2$,
l) —COOR, or
m) —((CH$_2$)$_m$O)$_n$R wherein m is 2, 3, 4 or 5 and n is zero, 1, 2 or 3, or 3) aryl, unsubstituted or substituted with one or more of
   a) halo,
   b) hydroxy,
   c) —NO$_2$ or —NR$_2$,
   d) C$_{1-4}$alkyl,
   e) C$_{1-3}$ alkoxy, unsubstituted or substituted with one or more of —OH or C$_{1-3}$ alkoxy,
   f) —COOR,
   g)

h) —CH$_2$NR$_2$, i)

j) —CN,
k) —CF$_3$,
l)

m) aryl C$_{1-3}$ alkoxy,
n) aryl,
o) —NRSO$_2$R,
p) —OP(O)(OR$_x$)$_2$, or
q) —R$^5$, as defined below; or 4) heterocycle unsubstituted or substituted with one or more of hydroxy, oxo, halo, amino, C$_{1-4}$ alkoxy, C$_{1-4}$ alkyl optionally substituted with hydroxy; or Boc;

5) carbocyclic unsubstituted or substituted with one or more of halo, amino, hydroxy or C$_{1-4}$ alkoxy;

R$^1$ and R$^2$ can be joined together to form with the nitrogen to which R$^1$ is attached a 3 to 10 membered monocyclic or bicyclic saturated ring system which consists of the nitrogen to which R$^1$ is attached and from 2 to 9 carbon atoms, and is unsubstituted or substituted with
1) hydroxy,
2) C$_{1-4}$ alkyl unsubstituted or substituted with one or more of
   a) halo,
   b) hydroxy,
   c) C$_{1-3}$ alkoxy,
   d) aryl,
   e) a 5-7 membered cycloalkyl group unsubstituted or substituted with one or more of
      i) halo,
      ii) hydroxy,
      iii) C$_{1-3}$ alkoxy, or
      iv) aryl,
   f) heterocycle, or
   g) —NR$_2$,
3) C$_{1-3}$ alkoxy,
4)

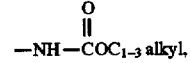

5)

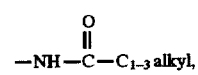

6) —NH—SO$_2$C$_{1-3}$alkyl,
7) heterocycle,
8) —W-aryl, or
9)

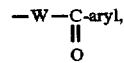

wherein W is as defined above; or

R$^1$ and R$^2$ can be joined together to form with the nitrogen to which R$^1$ is attached a 3 to 10 membered monocyclic or bicyclic saturated ring system which consists of the nitrogen to which $R^1$ is attached, from 1 to 8 carbon atoms and one or more unsubstituted or substituted heteroatom selected from 1) 

wherein V is absent or $$-\overset{O}{\underset{\|}{C}}-Q-$$

or $-SO_2-Q-$, $R^1$ is defined as above for when $R^1$ is independent from and not joined to $R^2$, and wherein Q is absent or $-O-$, $-NR-$, or heterocycle optionally substituted with $-C_{1-4}$alkyl, 2) 

3) 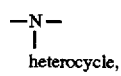

unsubstituted or substituted with aryl,

4) 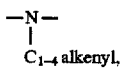

unsubstituted or substituted with aryl,
5) $-S(O)_p-$,
   wherein p is zero, 1 or 2, or
6) $-O-$; or
$R^1$ and $R^2$ can be joined together to form with the nitrogen to which $R^1$ is attached a 3 to 10 membered monocyclic or bicyclic saturated ring system, which consists of the nitrogen to which $R^1$ is attached and from 2 to 9 carbon atoms, in which the saturated ring system is fused to a phenyl ring and the phenyl ring is unsubstituted or substituted with one or more of
1) halo,
2) $C_{1-3}$ alkoxy,
3) hydroxy,
4) $C_{1-4}$ alkyl,
5) $-NHR^1$,
   wherein $R^1$ is defined as above for when $R^1$ is independent from and not joined to $R^2$, or
6) $-NH$-heterocycle;
$R^3$ is
1) $-(CH_2)_r-R^4$,
   wherein r is zero, 1, 2, 3, 4 or 5,
2) $C_{1-4}$alkenyl-$R^4$, or
3) $C_{1-4}$alkynyl-$R^4$;
$R^4$ is
1) hydrogen,
2) $C_{1-4}$ alkyl,
3) $C_5$–$C_{10}$ cycloalkyl, optionally substituted with hydroxy,
4) $C_6$–$C_{10}$ aryl, unsubstituted or substituted with one or more of a) halo,
b) hydroxy,
c) $-NO_2$ or $-NR^2$,
d) $C_{1-4}$alkyl,
e) $C_{1-3}$ alkoxy, unsubstituted or substituted with one or more of $-OH$ or $C_{1-3}$ alkoxy,
f) $-COOR$,
g) 

h) $-CH_2NR_2$,
i)

$$-CH_2NHCR,\ \overset{O}{\underset{\|}{}}$$

j) $-CN$,
k) $-CF_3$,
l)

$$-NHCR,\ \overset{O}{\underset{\|}{}}$$

m) aryl $C_{1-3}$ alkoxy,
n) aryl,
o) $-NRSO_2R$,
p) $-OP(O)(OR_x)_2$, or
q) $-R^5$, as defined below, or
5) monocyclic or bicyclic heterocyle containing from 1 to 3 heteroatoms chosen from the group consisting of N, O, and S and which is unsubstituted or substituted with $R^5$ and optionally with one or more of
a) halo,
b) $C_{1-4}$ alkyl, or
c) $C_{1-3}$ alkoxy;
$R_x$ is H or aryl;
$R^5$ is
1) $W-(CH_2)_m-NR^6R^7$
   wherein W is as defined above,
   m is 2, 3, 4 or 5, and
   $R^6$ and $R^7$ are independently
   a) hydrogen,
   b) $C_{1-6}$ alkyl, unsubstituted or substituted with one or more of
      i) $C_{1-3}$ alkoxy,
      ii) $-OH$, or
      iii) $-NR_2$.
   c) the same or different and joined together to form a 5–7 member heterocycle, such as morpholino, containing up to two additional heteroatoms selected from $$-\overset{R}{\underset{|}{N}}-,\ -O-,\ -\overset{O}{\underset{\|}{S}}-,$$

$-S-$, or $-SO_2-$, the heterocycle optionally substituted with $C_{1-4}$ alkyl, or
d) aromatic heterocycle unsubstituted or substituted with one or more of
   i) $C_{1-4}$ alkyl, or
   ii) $-NR_2$,
2) $-(CH_2)_q-NR^6R^7$ wherein q is 1, 2, 3, 4, or 5, and $R^6$ and $R^7$ are as defined above, except that $R^6_n$ or $R^7$ is not H or unsubstituted $C_{1-6}$ alkyl, or 3) benzofuryl, indolyl, azacycloalkyl, azabicyclo $C_{7-11}$ cycloalkyl, or benzopiperidinyl, unsubstituted or substituted with $C_{1-4}$ alkyl;

B is absent, or

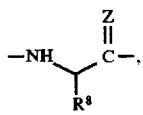

wherein $R^8$ is
1) —CH(CH$_3$)$_2$,
2) —CH(CH$_3$)(CH$_2$CH$_3$), or
3) -phenyl;

$J^1$ and $J^2$ are independently
1) —YR$^9$ wherein
 Y is —O— or —NH—, and
 R$^9$ is
  a) hydrogen,
  b) $C_{1-6}$ alkyl, unsubstituted or substituted with one or more of
   i) —NR$_2$,
   ii) —OR,
   iii) —NHSO$_2$C$_{1-4}$ alkyl,
   iv) —NHSO$_2$ aryl, or —NHSO$_2$ (dialkylaminoaryl),
   v) —CH$_2$OR,
   vi) —C$_{1-4}$ alkyl,
   vii)

viii)

ix)

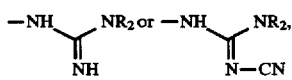

x)

wherein R$^{13}$ is
   A) —H,
   B) —C$_{1-4}$ alkyl,
   C) -aryl,
   D) -heterocycle, or
   E) —NH—, —O— or —(CH$_2$)n—
    wherein n is zero, 1, 2 or 3, substituted with
    I) —C$_{1-4}$ alkyl, unsubstituted or substituted with one or more of aryl or heterocycle, or
    II) aryl, unsubstituted or substituted with heterocycle,
   xi) —NR$_3^{\oplus}$A$^-$ wherein A$^-$ is a counterion,
   xii) —NR$^{10}$R$^{11}$ wherein R$^{10}$ and R$^{11}$ are the same or different and are $C_{1-5}$ alkyl joined together directly to form a 5–7 membered heterocycle containing up to one additional heteroatom selected from —O—, —S—, or —NR—,
   xiii) aryl,
   xiv) —CHO,
   xv) —OP(O)(OR$_x$)$_2$,
   xvi)

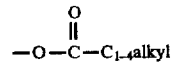

substituted with one or more of amine or quaternary amine, or —O—((CH$_2$)$_m$O)$_n$—R, or —OP(O)(OR$_x$)$_2$,
   xvii)

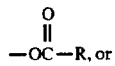

xviii)

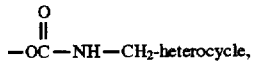

or
   c) —((CH$_2$)$_m$O)$_n$CH$_3$ or —((CH$_2$)$_m$O)$_n$H, wherein m and n are as defined above,
2) —N(R$^9$)$_2$,
3) —NR$^{10}$R$^{11}$ wherein R$^{10}$ and R$^{11}$ are as defined above, or
4)

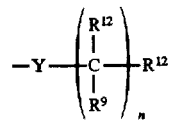

wherein Y, R$^9$ and n are defined above; and

R$^{12}$ is
1) hydrogen,
2) aryl, unsubstituted or substituted with one or more of
 a) R$^{14}$, wherein R$^{14}$ is
  i) halo,
  ii) —OR,
  iii)

iv) —CH$_2$NR$_2$,
  v) —SO$_2$NR$_2$,
  vi) —NR$_2$,
  vii)

viii) C$_{1-4}$ alkyl,
  ix) phenyl
  x) —CF$_3$, xi)

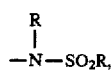

xii) —OP(O)(OR$_x$)$_2$, or xiii)

b) —C$_{1-4}$ alkyl-NR$_2$, or c)

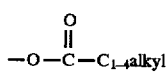

substituted with one or more of amine or quaternary amine or —OP(O)(OR$_x$)$_2$, 3) heterocycle, such as isochroman, chroman, isothiochroman, thiochroman, benzimidazole, benzothiopyran, oxobenzothiopyran, benzopyran, benzothiopyranylsulfone, benzothiopyranylsuffoxide, the ring or rings being unsubstituted or substituted with one or more of
 a) R$^{14}$, as defined above,
 b) —OC$_{1-4}$ alkenyl,
 c) phenyl-C$_{1-4}$ alkyl,
 d)

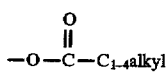

substituted with one or more of amine or quaternary amine, or —OP(O)(OR$_x$)$_2$, or —O((CH$_2$)$_m$O)$_n$—R, or e)

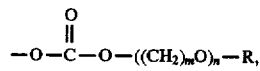

or

4) A 5 to 7 membered carbocyclic or 7–10 membered bicyclic carbocyclic ring, such as cyclopentane, cyclohexane, indane, norbornane, naphthalene, thiopyran, isothiopyran, or benzopyran, the carbocyclic ring being unsubstituted or substituted with one or more of
 a) R$^{14}$, as defined above,
 b) —CH$_2$OR,
 c) —(CH$_2$)$_n$—NR$_2$, C$_{5-16}$alkyl, pyridine, CH$_2$)$_n$NR—(CH$_2$)$_n$—NR$_2$,

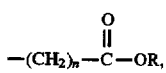

—((CH$_2$)$_m$O)$_n$—R, quinuclidiniumyl substituted with R, piperazine-C$_{1-4}$alkyl-benzyl substituted once or more with R, or morpholino-C$_{1-4}$alkyl-benzyl, d)

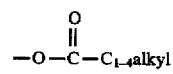

substituted with one or more of amine or quaternary amine, —OP(O)(OR$_x$)$_2$, or —O—((CH$_2$)$_m$O)$_n$—R, e)

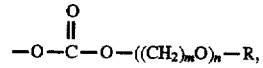

or f) —C$_{1-4}$alkyl-phenyl;

or a pharmaceutically acceptable salt thereof.

In one embodiment of this invention, both A and D are —CH$_2$—.

In a preferred embodiment of this invention, both A and D are —CH$_2$— and R$^1$ and R$_2$ are joined together to form with the nitrogen to which R$^1$ is attached a 3 to 10 membered monocyclic or bicyclic saturated ring system which consists of the nitrogen to which R$^1$ is attached and from 2 to 9 carbon atoms, and is unsubstituted or substituted with
 1) hydroxy,
 2) C$_{1-4}$ alkyl unsubstituted or substituted with one or more of
  a) hydroxy,
  b) C$_{1-3}$ alkoxy,
  c) aryl,
  d) a 5–7 membered cycloalkyl group unsubstituted or substituted with one or more of
   i) halo,
   ii) hydroxy,
   iii) C$_{1-3}$ alkoxy, or
   iv) aryl,
  e) heterocycle, or
  f) —NR$_2$,
 3) C$_{1-3}$ alkoxy,
 4)

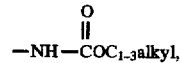

5)

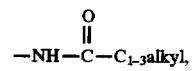

6) —NH—SO$_2$C$_{1-3}$alkyl,

7) —W-aryl, or

8)

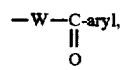

wherein W is —O—, —S—, or —NH—; or

R$^1$ and R$^2$ are joined together to form with the nitrogen to which R$^1$ is attached a 3 to 10 membered monocyclic or bicyclic saturated ring system which consists of the nitrogen to which R$^1$ is attached, from 1 to 8 carbon atoms and one or more unsubstituted or substituted heteroatom selected from

1)

wherein V is absent or

or —SO$_2$—Q—, R$^1$ is defined as above for when R$^1$ is independent from and not joined to R$^2$, and wherein Q is absent or —O—, —NR—, or heterocycle optionally substituted with —C$_{1-4}$alkyl,

2)

unsubstituted or substituted with aryl,

3) —S(O)$_p$—, wherein p is zero, 1 or 2, or

4) —O—; or

R$^1$ and R$^2$ are joined together to form with the nitrogen to which R$^1$ is attached a 3 to 10 membered monocyclic or bicyclic saturated ring system, which consists of the nitrogen to which R$^1$ is attached and from 2 to 9 carbon atoms, in which the saturated ring system is fused to a phenyl ring and the phenyl ring is unsubstituted or substituted with one or more of 1) C$_{1-3}$ alkoxy,
2) hydroxy,
3) C$_{1-4}$ alkyl, or
4) —NHR$^1$, wherein R$^1$ is defined as above for when R$^1$ is independent from and not joined to R$^2$.

A second, more preferred embodiment of this invention is further limited to compounds wherein A and D are both —CH$_2$— and R$^1$ and R$^2$ are joined together to form with the nitrogen to which R$^1$ is attached a 3 to 10 membered monocyclic or bicyclic saturated ring system which consists of the nitrogen to which R$^1$ is attached and from 2 to 9 carbon atoms, and is unsubstituted or substituted with 1) hydroxy,
2) C$_{1-4}$ alkyl unsubstituted or substituted with one or more of
   a) hydroxy,
   b) C$_{1-3}$ alkoxy,
   c) aryl,
   d) a 5–7 membered cycloalkyl group unsubstituted or substituted with one or more of
      i) halo,
      ii) hydroxy,
      iii) C$_{1-3}$ alkoxy, or
      iv) aryl,
   e) heterocycle, or
   f) —NR$_2$,
3) C$_{1-3}$ alkoxy,

4)

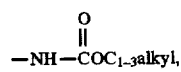

5)

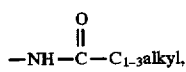

6) —NH—SO$_2$C$_{1-3}$alkyl,
7) —W-aryl, or
8)

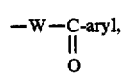

wherein W is —O—, —S—, or —NH—; or

R$^1$ and R$^2$ are joined together to form with the nitrogen to which R$^1$ is attached a 3 to 10 membered monocyclic or bicyclic saturated ring system which consists of the nitrogen to which R$^1$ is attached, from 1 to 8 carbon atoms and one or more unsubstituted or substituted heteroatom selected from

1)

wherein V is absent or

or —SO$_2$—Q—, R$^1$ is defined as above for when R$^1$ is independent from and not joined to R$^2$, and wherein Q is absent or —O—, —NR—, or heterocycle optionally substituted with —C$_{1-4}$alkyl, 2) —S(O)$_p$—, wherein p is zero, 1 or 2, or

3) —O—;

R$^3$ is benzyl, unsubstituted or substituted with one or more of a) hydroxy,
b) —NO$_2$, or —NR$_2$,
c) C$_{1-4}$alkyl,
d) C$_{1-3}$ alkoxy, unsubstituted or substituted with one or more of —OH or C$_{1-3}$ alkoxy,
e)

f) —CH$_2$NR$_2$,
g)

h) —CF$_3$, i)

j) —NRSO$_2$R, k) —OP(O)(OR$_x$)$_2$, or l) —R$^5$;

and B is absent.

A third, most preferred embodiment of this invention is further limited to compounds wherein A and D are both —CH$_2$— and X is —OH;

Z is —O;

R$^1$ and R$^2$ are joined together to form with the nitrogen to which R$^1$ is attached a 3 to 10 membered monocyclic or bicyclic saturated ring system which consists of the nitrogen to which R$^1$ is attached and from 2 to 9 carbon atoms, and is unsubstituted or substituted with —W-aryl or

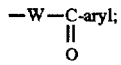

or

R$^1$ and R$^2$ are joined together to form with the nitrogen to which R$^1$ is attached a 3 to 10 membered monocyclic or bicyclic saturated ring system which consists of the nitrogen to which R$^1$ is attached, from 1 to 8 carbon atoms and one of

wherein V is absent or

or —SO$_2$—Q—,

R$^1$ is defined as above for when R$^1$ is independent from and not joined to R$^2$, that is, R$^1$ is 1) hydrogen, 2) —C$_{1-4}$ alkyl unsubstituted or substituted with one or more of
 a) halo,
 b) hydroxy,
 c) C$_{1-3}$ alkoxy,
 d) aryl unsubstituted or substituted with one or more of C$_{1-4}$alkyl, amino, hydroxy or aryl,
 e) —W-aryl or —W-benzyl, wherein W is —O—, —S—, or —NH—,
 f) a 5–7 membered cycloalkyl group unsubstituted or substituted with one or more of
  i) halo,
  ii) hydroxy,
  iii) C$_{1-3}$ alkoxy, or
  iv) aryl,
 g) heterocycle unsubstituted or substituted with one or more of hydroxy, oxo, halo, C$_{1-4}$ alkoxy, C$_{1-4}$alkyl optionally substituted with hydroxy;

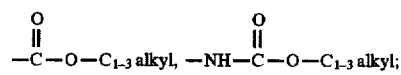

or Boc, h)

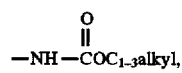

i)

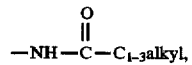

j) —NH—SO$_2$C$_{1-3}$alkyl, k) —NR$_2$, l) —COOR, or m) —((CH$_2$)$_m$O)$_n$R wherein m is 2, 3, 4 or 5 and n is zero, 1, 2 or 3, or 3) aryl, unsubstituted or substituted with one or more of
 a) halo,
 b) hydroxy,
 c) —NO$_2$ or —NR$_2$,
 d) C$_{1-4}$alkyl,
 e) C$_{1-3}$ alkoxy, unsubstituted or substituted with one or more of —OH or C$_{1-3}$ alkoxy,
 f) —COOR,
 g)

h) —CH$_2$NR$_2$, i)

j) —CN, k) —CF$_3$, l)

m) aryl C$_{1-3}$ alkoxy, n) aryl, o) —NRSO$_2$R, p) —OP(O)(OR$_x$)$_2$, or q) —R$^5$, or 4) heterocycle unsubstituted or substituted with one or more of hydroxy, oxo, halo, amino, C$_{1-4}$ alkoxy, C$_{1-4}$ alkyl optionally substituted with hydroxy; or Boc;

5) carbocyclic unsubstituted or substituted with one or more of halo, amino, hydroxy or C$_{1-4}$ alkoxy;

and wherein Q is absent or —O—, —NR— or heterocycle optionally substituted with —C$_{1-4}$alkyl;

R$^3$ is benzyl, unsubstituted or substituted with one or more of (1) hydroxy, (2) C$_{1-3}$ alkoxy substituted with one or more of —OH or (3)

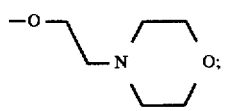

$J^1$ is —NH—$C_{1-4}$alkyl; and $J^2$ is

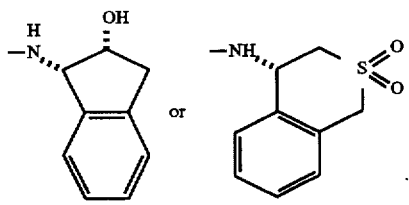

The most preferred compounds of this invention are compounds A through H and J, shown below.

Compound A

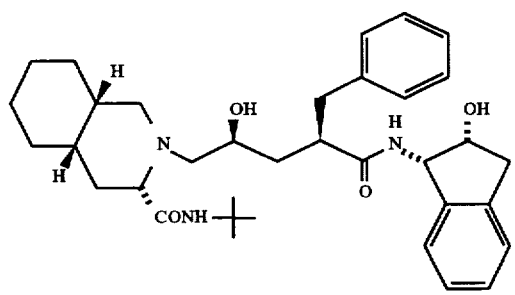

N-(2(R)-hydroxy-1(S)-indanyl)-2(R)-phenylmethyl-4(S)-hydroxy-5-(2-(3(S)-N'-(t-butylcarbamoyl)-(4aS,8aS)-decahydroisoquinoline)yl)-pentaneamide, Compound B

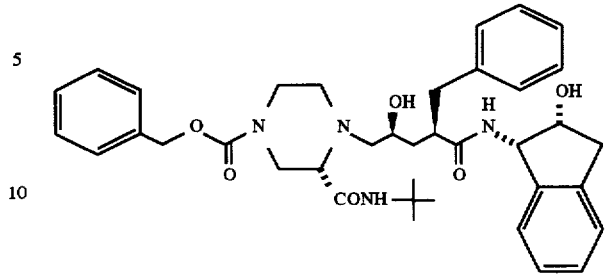

N-(2(R)-hydroxy-1(S)-indanyl)-2(R)-phenylmethyl-4(S)-hydroxy-5-(1-(4-carbobenzyloxy-2(S)-N'-(t-butylcarbamoyl)-piperazinyl))-pentaneamide, Compound C

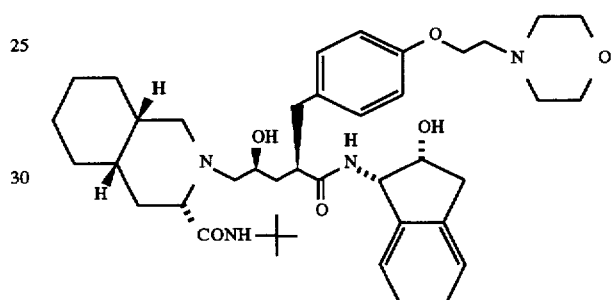

N-(2(R)-hydroxy-1(S)-indanyl)-2(R)-((4-(2-(4-morpholinyl)ethoxy)phenyl)methyl)-4(S)-hydroxy-5-(2-(3(S)-N'-(t-butylcarbamoyl)-(4aS,8aS)-decahydroisoquinoline)yl)-pentaneamide, Compound D

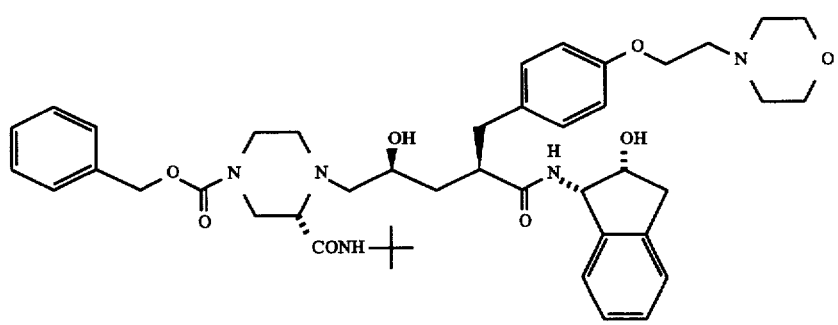

N-(2(R)-hydroxy-1(S)-indanyl)-2(R)-((4-(2-(4-morpholinyl)ethoxy)phenyl)methyl)-4(S)-hydroxy-5-(1-(4-carbobenzyloxy-2(S)-N'-(t-butylcarbamoyl)-piperazinyl))-pentaneamide, Compound E

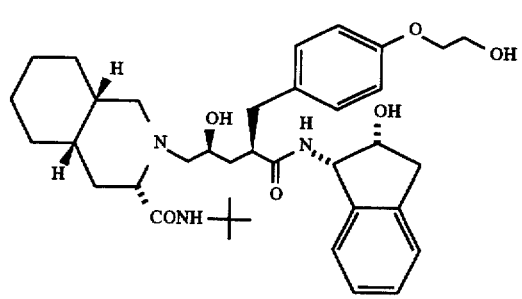

N-(2(R)-hydroxy-1(S)-indanyl)-2(R)-((4-((2-hydroxy)-ethoxy)phenyl)methyl)-4(S)-hydroxy-5-(2-(3(S)-N'-(t-butylcarbamoyl)-(4aS,8aS)-decahydroisoquinoline)-yl)-pentaneamide, Compound F

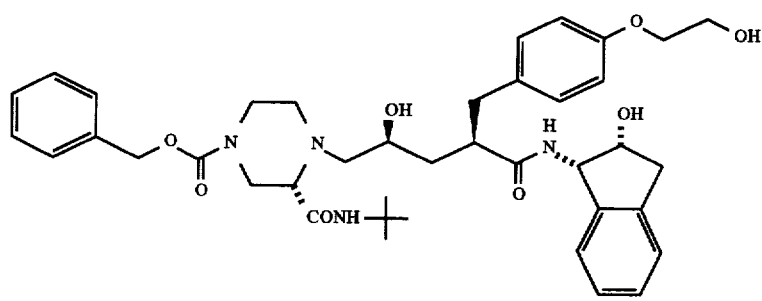

N-(2(R)-hydroxy-1(S)-indanyl)-2(R)-((4-((2-hydroxy)-ethoxy)phenyl)methyl)-4(S)-hydroxy-5-(1-(4-carbobenzyloxy-2(S)-N'-(t-butylcarbamoyl)-piperazinyl))-pentaneamide, Compound G

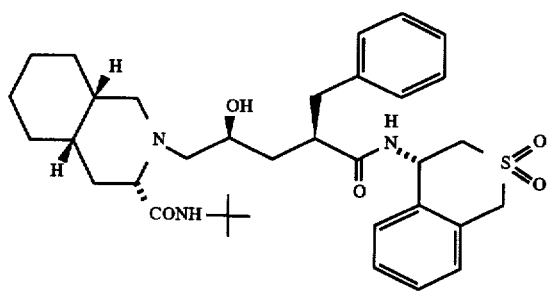

N-(4(S)-3,4-dihydro-1H-2,2-dioxobenzothiopyranyl)-2(R)-phenylmethyl-4(S)-hydroxy-5-(2-(3(S)-N'-(t-butylcarbamoyl)-(4aS,8aS)-decahydroisoquinoline)yl)-pentaneamide, Compound H

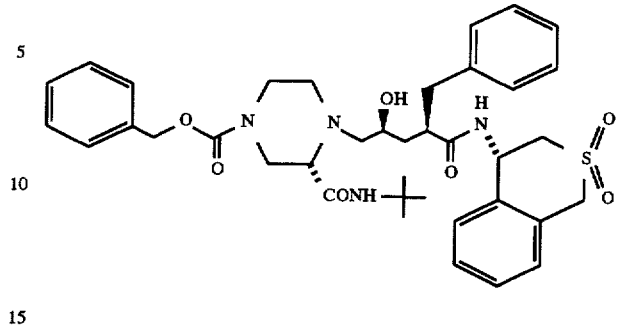

N-(4(S)-3,4-dihydro-1H-2,2-dioxobenzothiopyranyl)-2(R)-phenylmethyl-4(S)-hydroxy-5-(1-(4-carbobenzyloxy-2(S)-N'-(t-butylcarbamoyl)-piperazinyl))-pentaneamide, Compound J: (L-735,524)

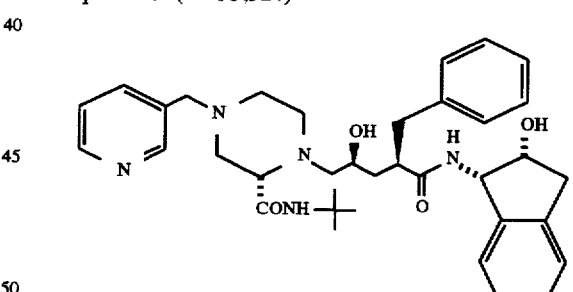

N-(2(R)-hydroxy-1(S)-indanyl)-2(R)-phenylmethyl-4(S)-hydroxy-5-(1-(4-(3-pyridylmethyl)-2(S)-N'-(t-butylcarbamoyl)-piperazinyl))-pentaneamide; alternatively named

[1S-[1α[αS*, γR*, δ(R*)], 2α]]-N-(2,3-dihydro-2-hydroxy-1H-inden-1-yl)-2-[[(1,1-dimethylethyl)amino]carbonyl]-γ-hydroxy-α-(phenylmethyl)-4-(3-pyridinylmethyl)-1-piperazinepentaneamide; alternatively named N-(1(S)-2,3-dihydro-2(R)-hydroxy-1H-indenyl)-4(S)-hydroxy-2(R)-phenylmethyl-5-[4-(3-pydridylmethyl)-2(S)-(t-butylcarbamoyl)piperazinyl]pentaneamide; alternatively named

[1S-[1α(R*), 2α]]-2,3,5-trideoxy-N-(2,3-dihydro-2-hydroxy-1

H-inden-1-yl)-5-[2-[[(1,1-dimethylethyl)amino]carbonyl]-4-(3-pyridinylmethyl)-1-piperazinyl]-2-(phenylmethyl-D-erythro-pentanamide, or pharmaceutically acceptable salt of any of these compounds.

Novel compounds of the present invention also include but are not limited to the following compounds:

N-(2(R)-hydroxy-1(S)-indanyl)-2(R)-phenylmethyl-4-(S)-hydroxy-5-(1-(N'-(t-butyl)-4(S)-phenoxyprolineamid)yl)-pentaneamide, N-(2(R)-hydroxy-1(S)-indanyl)-2(R)-phenylmethyl-4-(S)-hydroxy-5-(1-(N'-t-butyl-4(S)-2-naphthyloxyprolineamid)yl)-pentaneamide, N-(2(R)-hydroxy-1(S)-indanyl)-2(R)-phenylmethyl-4-(S)-hydroxy-5-(1-(N'-t-butyl-4(S)-1-naphthyloxyprolineamid)yl)-pentaneamide, N-(2(R)-hydroxy-1(S)-indanyl)-2(R)-phenylmethyl-4-(S)-amino-5-(2-(3(S)-N'-(t-butylcarbamoyl)-(4aS,8aS)-decahydroisoquinoline)yl)pentaneamide, N-(2(R)-hydroxy-1(S)-indanyl)-2(R)-phenylmethyl-4-(S)-hydroxy-5-(1-(4-(3-phenylpropionyl)-2(S)-N'-(t-butylcarbamoyl)-piperazinyl))-pentaneamide, N-(2(R)-hydroxy-1(S)-indanyl)-2(R)-phenylmethyl-4-(S)-hydroxy-5-(1-(4-benzoyl-2(S)-N'-(t-butylcarbamoyl)-piperazinyl))-pentaneamide, N-(2(R)-hydroxy-1(S)-indanyl)-2(R)-phenylmethyl-4-(S)-hydroxy-5-(1-(4-(3-phenylpropyl)-2(S)-N'-(t-butylcarbamoyl)-piperazinyl))-pentaneamide, N-(2(R)-hydroxy-1(S)-indanyl)-2(R)-phenylmethyl-4-(S)-amino-5-(1-(4-carbobenzyloxy-2(S)-N'-(t-butylcarboxamido)-piperazinyl))-pentaneamide, N-(2(R)-hydroxy-1(S)-indanyl)-2(R)-((4-(2-(4-morpholinyl)ethoxy)phenyl)methyl)-4(S)-hydroxy-5-(1-(N'-(t-butyl)-4(S)-phenoxyprolineamid)yl)-pentaneamide, N-(2(R)-hydroxy-1(S)-indanyl)-2(R)-((4-(2-(4-morpholinyl)ethoxy)phenyl)methyl)-4(S)-hydroxy-5-(1-(N'-t-butyl-4(S)-2-naphthyloxyprolineamid)yl)-pentaneamide, N-(2(R)-hydroxy-1(S)-indanyl)-2(R)-((4-(2-(4-morpholinyl)ethoxy)phenyl)methyl)-4(S)-hydroxy-5-(1-(N'-t-butyl-4(S)-1-naphthyloxyprolineamid)yl)-pentaneamide, N-(2(R)-hydroxy-1(S)-indanyl)-2(R)-((4-(2-(4-morpholinyl)ethoxy)phenyl)methyl)-4(S)-amino-5-(2-(3(S)-N'-(t-butylcarbamoyl)-(4aS,8aS)-decahydroisoquinoline)yl)-pentaneamide, N-(2(R)-hydroxy-1(S)-indanyl)-2(R)-((4-(2-(4-morpholinyl)ethoxy)phenyl)methyl)-4(S)-hydroxy-5-(1-(4-(3-phenylpropionyl)-2(S)-N'-(t-butylcarbamoyl)piperazinyl))-pentaneamide, N-(2(R)-hydroxy-1(S)-indanyl)-2(R)-((4-(2-(4-morpholinyl)ethoxy)phenyl)methyl)-4(S)-hydroxy-5-(1-(4-benzoyl-2(S)-N'-(t-butylcarbamoyl)-piperazinyl))-pentaneamide, N-(2(R)-hydroxy-1(S)-indanyl)-2(R)-((4-(2-(4-morpholinyl)ethoxy)phenyl)methyl)-4(S)-hydroxy-5-(1-(4-(3-phenylpropyl)-2(S)-N'-(t-butylcarbamoyl))-piperazinyl)-pentaneamide, N-(2(R)-hydroxy-1(S)-indanyl)-2(R)-((4-(2-(4-morpholinyl)ethoxy)phenyl)methyl)-4(S)-amino-5-(1-(4-carbobenzyloxy-2(S)-N'-(t-butylcarbamoyl)-piperazinyl)pentaneamide, N-(2(R)-hydroxy-1(S)-indanyl)-2(R)-((4-((2-hydroxy)ethoxy)phenyl)methyl)-4(S)-hydroxy-5-(1-(N'-(t-butyl)-4(S)-phenoxyprolineamid)yl)-pentaneamide, N-(2(R)-hydroxy-1(S)-indanyl)-2(R)-((4-((2-hydroxy)ethoxy)phenyl)methyl)-4(S)-hydroxy-5-(1-(N'-t-butyl-4(S)-2-naphthyloxy-prolineamid)yl)-pentaneamide, N-(2(R)-hydroxy-1(S)-indanyl)-2(R)-((4-((2-hydroxy)ethoxy)phenyl)methyl)-4(S)-hydroxy-5-(1-(N'-t-butyl-(S)-1-naphthyloxy-prolineamid)yl)-pentaneamide, N-(2(R)-hydroxy-1(S)-indanyl)-2(R)-((4-((2-hydroxy)ethoxy)phenyl)methyl)-4(S)-amino-5-(2-(3(S)-N'-(t-butylcarbamoyl)-(4aS,8aS)-decahydroisoquinoline)yl)-pentaneamide, N-(2(R)-hydroxy-1(S)-indanyl)-2(R)-((4-((2-hydroxy)-ethoxy)phenyl)methyl)-4(S)-hydroxy-5-(1-(4-(3-phenyl-propionyl)-2(S)-N'-(t-butylcarbamoyl)-piperazinyl))-pentaneamide, N-(2(R)-hydroxy-1(S)-indanyl)-2(R)-((4-((2-hydroxy)ethoxy)-phenyl)methyl)-4(S)-hydroxy-5-(1-(4-benzoyl-2(S)-N'-(t-butylcarbamoyl)-piperazinyl))-pentaneamide, N-(2(R)-hydroxy-1(S)-indanyl)-2(R)-((4-((2-hydroxy)ethoxy)phenyl)methyl)-4(S)-hydroxy-5-(1-(4-(3-phenylpropyl)-2(S)-N'-(t-butylcarbamoyl))-piperazinyl)-pentaneamide, N-(2(R)-hydroxy-1(S)-indanyl)-2(R)-((4-((2-hydroxy)ethoxy)phenyl)methyl)-4(S)-amino-5-(1-(4-carbobenzyloxy-2(S)-N'-(t-butylcarbamoyl)-piperazinyl))-pentaneamide, N-(4(S)-3,4-dihydro-1H-2,2-dioxobenzothiopyranyl)-2(R)-phenylmethyl-4(S)-hydroxy-5-(1-(N'-(t-butyl)-4(S)-phenoxyprolineamid)yl)-pentaneamide, N-(4(S)-3,4-dihydro-1H-2,2-dioxobenzothiopyranyl)-2-(R)-phenylmethyl-4(S)-hydroxy-5-(1-(N'-t-butyl-4(S)-2-naphthyloxy-prolineamid)yl)-pentaneamide, N-(4(S)-3,4-dihydro-1H-2,2-dioxobenzothiopyranyl)-2-(R)-phenylmethyl-4(S)-hydroxy-5-(1-(N'-t-butyl-4(S)-1-naphthyloxy-prolineamid)yl)-pentaneamide, N-(4(S)-3,4-dihydro-1H-2,2-dioxobenzothiopyranyl)-2-(R)-phenyl-methyl-4(S)-amino-5-(2-(3(S)-N'-(t-butylcarbamoyl)-(4aS,8aS)-decahydroisoquinoline)yl)-pentaneamide, N-(4(S)-3,4-dihydro-1H-2,2-dioxobenzothiopyranyl)-2-(R)-phenylmethyl-4(S)-hydroxy-5-(1-(4-(3-phenylpropionyl)-2(S)-N'-(t-butylcarbamoyl)-piperazinyl))-pentaneamide, N-(4(S)-3,4-dihydro-1H-2,2-dioxobenzothiopyranyl)-2-(R)-phenylmethyl-4(S)-hydroxy-5-(1-(4-benzoyl-2(S)-N'-(t-butylcarbamoyl)-piperazinyl))-pentaneamide, N-(4(S)-3,4-dihydro-1H-2,2-dioxobenzothiopyranyl)-2-(R)-phenylmethyl-4(S)-hydroxy-5-(1-(4-(3-phenylpropyl)-2(S)-N'-(t-butylcarbamoyl))-piperazinyl)-pentaneamide, or (4(S)-3,4-dihydro-1H-2,2-dioxobenzothiopyranyl)-2(R)-phenylmethyl-4(S)-amino-5-(1-(4-carbobenzyloxy-2(S)-N'-(t-butylcarbamoyl)-piperazinyl))-pentaneamide.

Another embodiment of the present invention are compounds of the formula

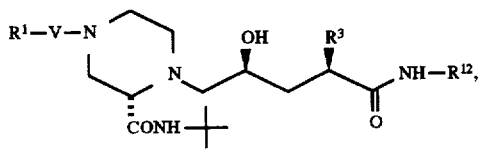

or pharmaceutically acceptable salt thereof, wherein $R^1$ is not H, nor substituted with OH.

Another embodiment of this invention are compounds of the formula

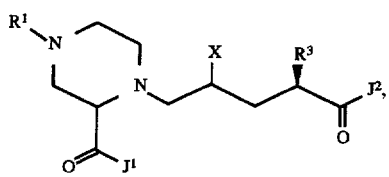

wherein

X=OH or NH₂;

R¹ is C₁₋₄ alkyl substituted with pyridyl or aryl;

R³ is benzyl, unsubstituted or substituted with one or more of (1) hydroxy, (2) C₁₋₃ alkoxy substituted with one or more of —OH or (3)

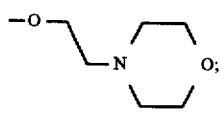

J¹ is —NH—C₁₋₄ alkyl; and

J² is

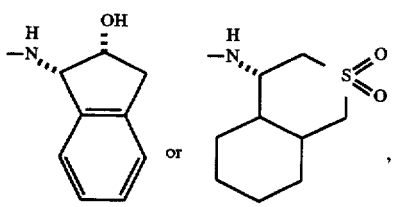

or pharmaceutically acceptable salt thereof.

Another embodiment of this invention are compounds of the formula

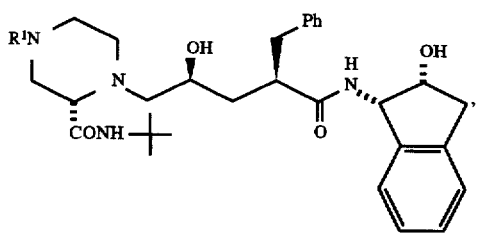

or pharmaceutically acceptable salt thereof, wherein R¹ is selected from

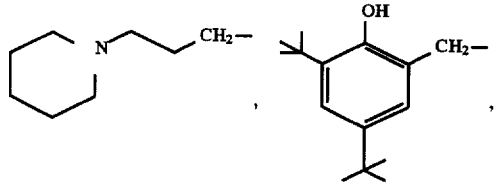

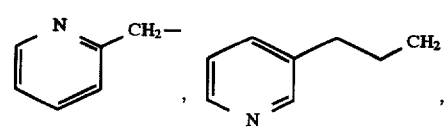

-continued

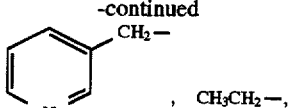

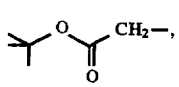, CH₃CH₂—,

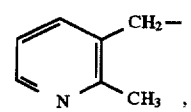

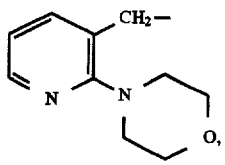,

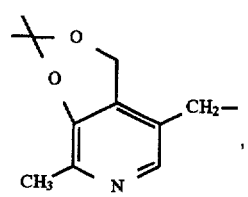

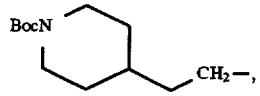

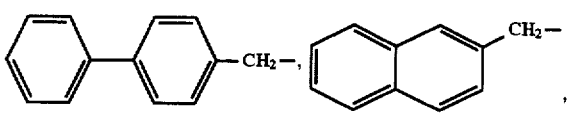

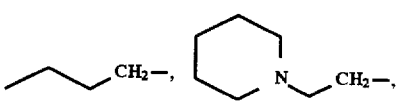

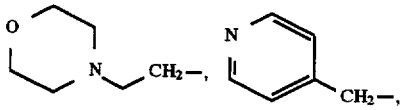

CH₃O(CH₂CH₂O)₂—CH₂CH₂—,

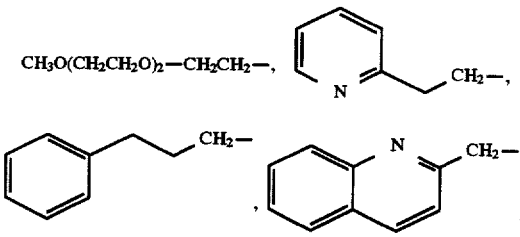

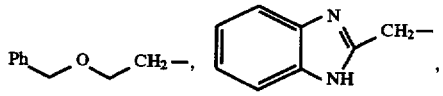

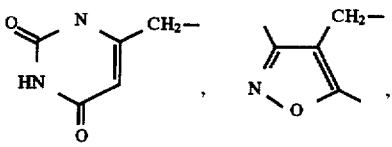

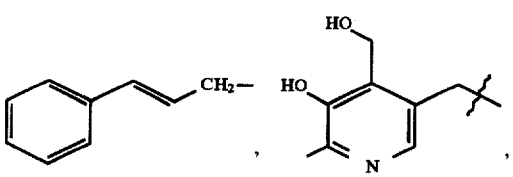

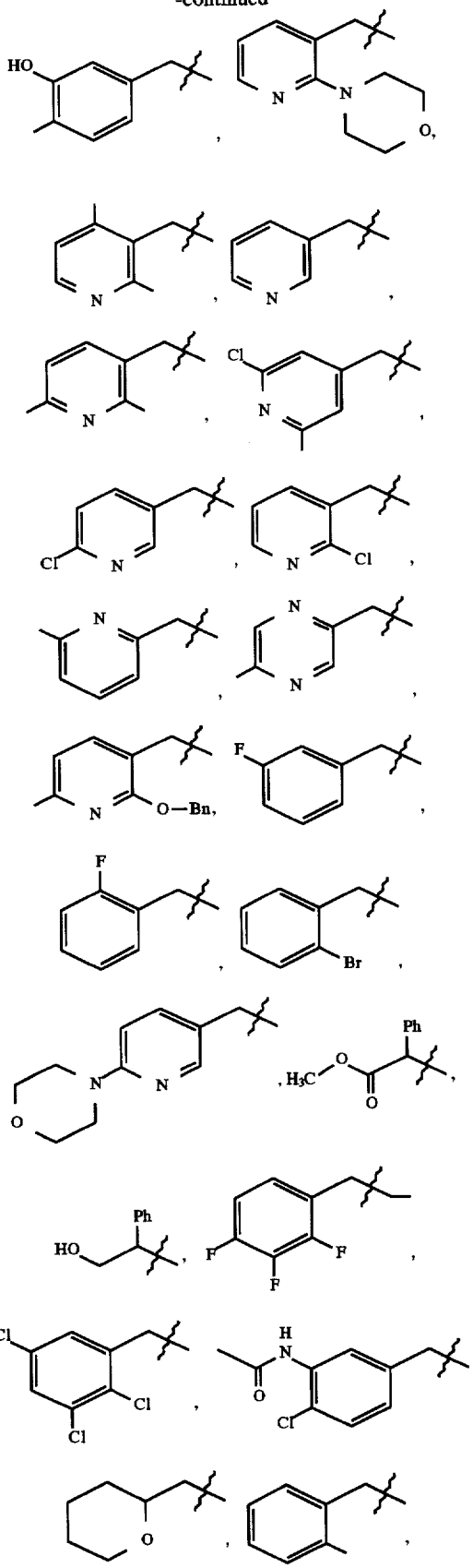
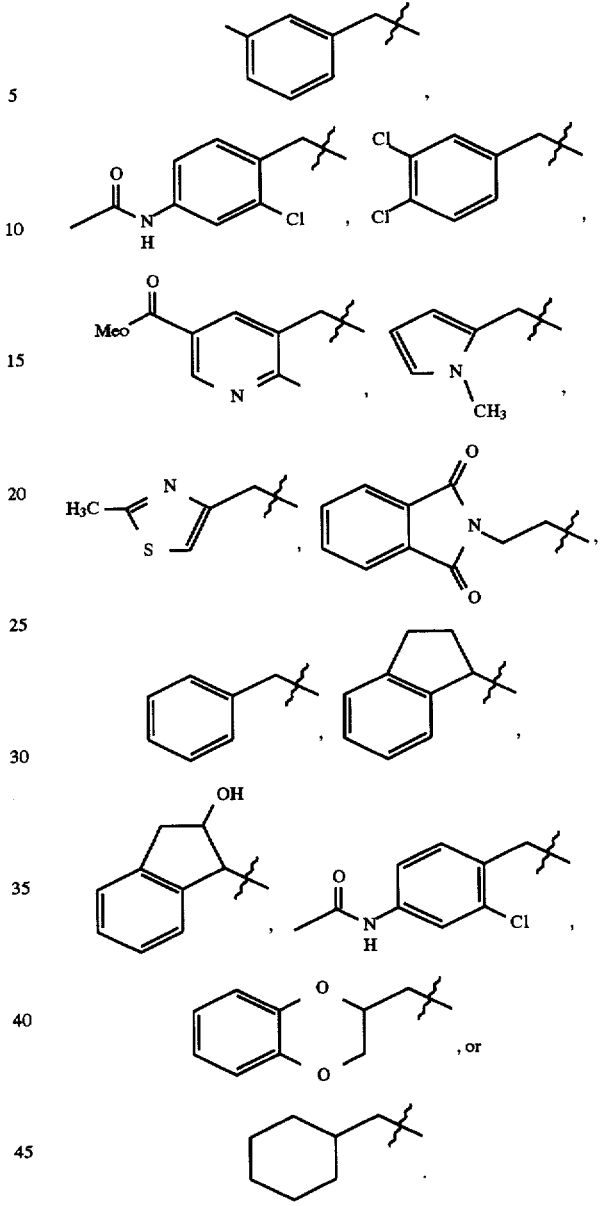

The compounds of the present invention, may have asymmetric centers and occur as racemates, racemic mixtures and as individual diastereomers, or enantiomers with all isomeric forms being included in the present invention.

When any variable (e.g., aryl, heterocycle, R, $R^1$, $R^2$, $A^-$, n, Z, etc.) occurs more than one time in any constituent or in Formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge; and "cycloalkyl" is intended to include saturated ring groups, such as cyclopropyl, cyclobutyl, cyclopentyl, cyclohexyl (Cyh) and cycloheptyl. "Alkenyl" is intended to include hydrocarbon groups of either a straight or branched configuration with one or more carbon-carbon double bonds which may occur in any stable point along the chain, such as ethenyl, propenyl, butenyl, pentenyl, and the like. "Alkynyl" is intended to include hydrocarbon groups of either a straight or branched configuration with one or more carbon-carbon triple bonds which may occur in any stable point along the chain, such as ethynyl, propynyl, butynyl, pentynyl, and the like. "Halo", as used herein, means fluoro, chloro, bromo and iodo; and "counterion" is used to represent a small, single negatively-charged species, such as chloride, bromide, hydroxide, acetate, trifluroacetate, perchlorate, nitrate, benzoate, maleate, tartrate, hemitartrate, benzene sulfonate, and the like.

As used herein, with exceptions as noted, "aryl" is intended to mean phenyl (Ph) or naphthyl. "Carbocyclic" is intended to mean any stable 5- to 7-membered carbon ring or 7- to 10-membered bicyclic carbon ring any ring of which may be saturated or unsaturated.

The term heterocycle or heterocyclic, as used herein except where noted, represents a stable 5- to 7-membered mono- or bicyclic or stable 7- to 10-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic tings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

Schemes I–III for preparing the novel compounds of this invention are presented below. Tables I and II which follow the schemes illustrate the compounds that can be synthesized by Schemes I–III, but Schemes I–III are not limited by the compounds in the tables nor by any particular substituents employed in the schemes for illustrative purposes. The examples specifically illustrate the application of the following schemes to specific compounds.

Amide couplings used to form the compounds of this invention are typically performed by the carbodiimide method with reagents such as dicyclohexylcarbodiimide, or 1-ethyl-3-(3-dimethylaminopropyl) carbodiimide. Other methods of forming the amide or peptide bond include, but are not limited to the synthetic routes via an acid chloride, azide, mixed anhydride or activated ester. Typically, solution phase amide coupling are performed, but solid-phase synthesis by classical Merrifield techniques may be employed instead. The addition and removal of one or more protecting groups is also typical practice.

Additional related information on synthetic background is contained in EPO 0337714.

One method for producing Formula I compounds is provided by Scheme I. Dihydro-5(S)-(tert-butyldimethylsilyloxymethyl)-3(2H)-furanone (compound 1 below) is prepared by standard methods known in the art from commercially available dihydro-5(S)-(hydroxymethyl)-2(3H)-furanone. After alkylation of compound 1 to form compound 2, the protecting group of lactone 2 is removed with aqueous HF to afford compound 3.

The alcohol group of 3 is activated by conversion into a leaving group such as mesylate, tosylate or trifylate by treating the alcohol with a sulfonyl chloride or sulfonic anhydride, such as trifluoromethanesulfonic anhydride, in the presence of a hindered amine base such as triethylamine, diethyl isopropylamine or 2,6 lutidine, to afford a compound such as compound 4. The leaving group of compound 4 is displaced by an amine 5, such as N'-t-butyl-(4aS,8aS)-(decahydroisoquinoline)-3(S)-carboxamide, in a high boiling solvent such as DMF or xylene to produce a compound such as 6. A trifluoromethanesulfonyloxy group can be displaced by an amine at room temperature in a solvent such as isopropanol by treatment with N,N-diisopropylethylamine.

Compound 6 is hydrolyzed with aqueous lithium or sodium hydroxide and the resultant hydroxy acid 7 is converted into a protected hydroxy acid 8. The hydroxyl group is conveniently protected with a standard silyl protecting group such as t-butyldimethyl silyl or t-butyldiphenyl silyl.

The protected hydroxy-acid 8 is then coupled to the desired $R^{12}$ amine to produce compound 9, and the silyl protecting group is removed with fluoride ion to arrive at compound 10.

SCHEME I

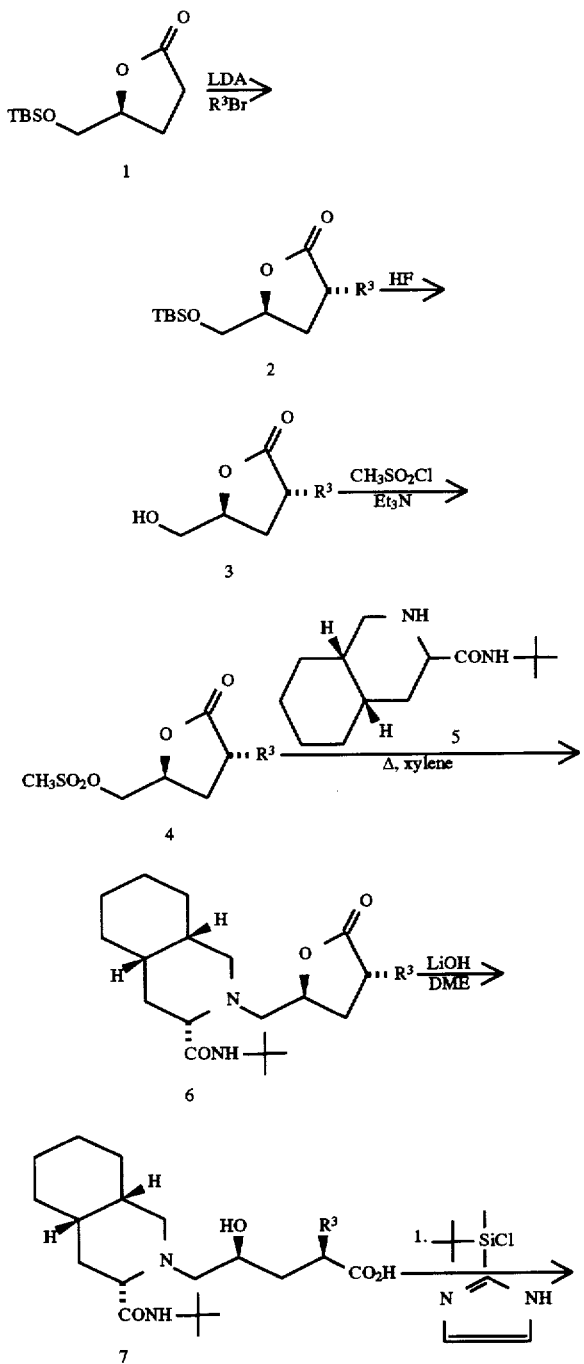

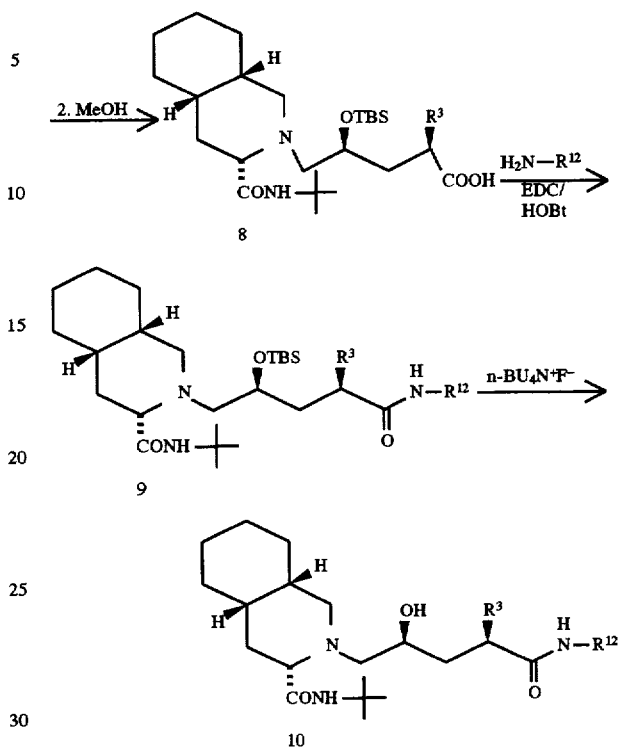

A second method for forming products of general Formula I is shown in Scheme II. In Scheme II, alkylation of 11 is performed by a first step of deprotonation of 11 with n-butyllithium or lithium diisopropylamide (LDA) followed by a second step of adding an alkenyl halide (such as allyl bromide) to afford 12.

Dihydroxylation of the olefin of 12 with osmium tetroxide and N-methylmorpholine-N-oxide (NMO) produces a diasteriomeric mixture of diols, 13. Selective mesylation of the primary alcohol of 13 with methanesulfonyl chloride and either triethylamine or pyridine gives a mesylate 14.

Heating mesylate 14 with an amine in a refluxing alcoholic solvent such as methanol or isopropanol which contains an excess of potassium carbonate produces an amino alcohol such as compound 15. The diasteriomers can be separated at this step by standard techniques well known to those of skill in the art. Alternatively, the separation can be done after removal of the ketal.

Removal of the ketal in compound 15 is accomplished by treatment with acid in the presence of methanol, or by aqueous acid or by 1N HCl in THF, to form compound 16.

SCHEME II

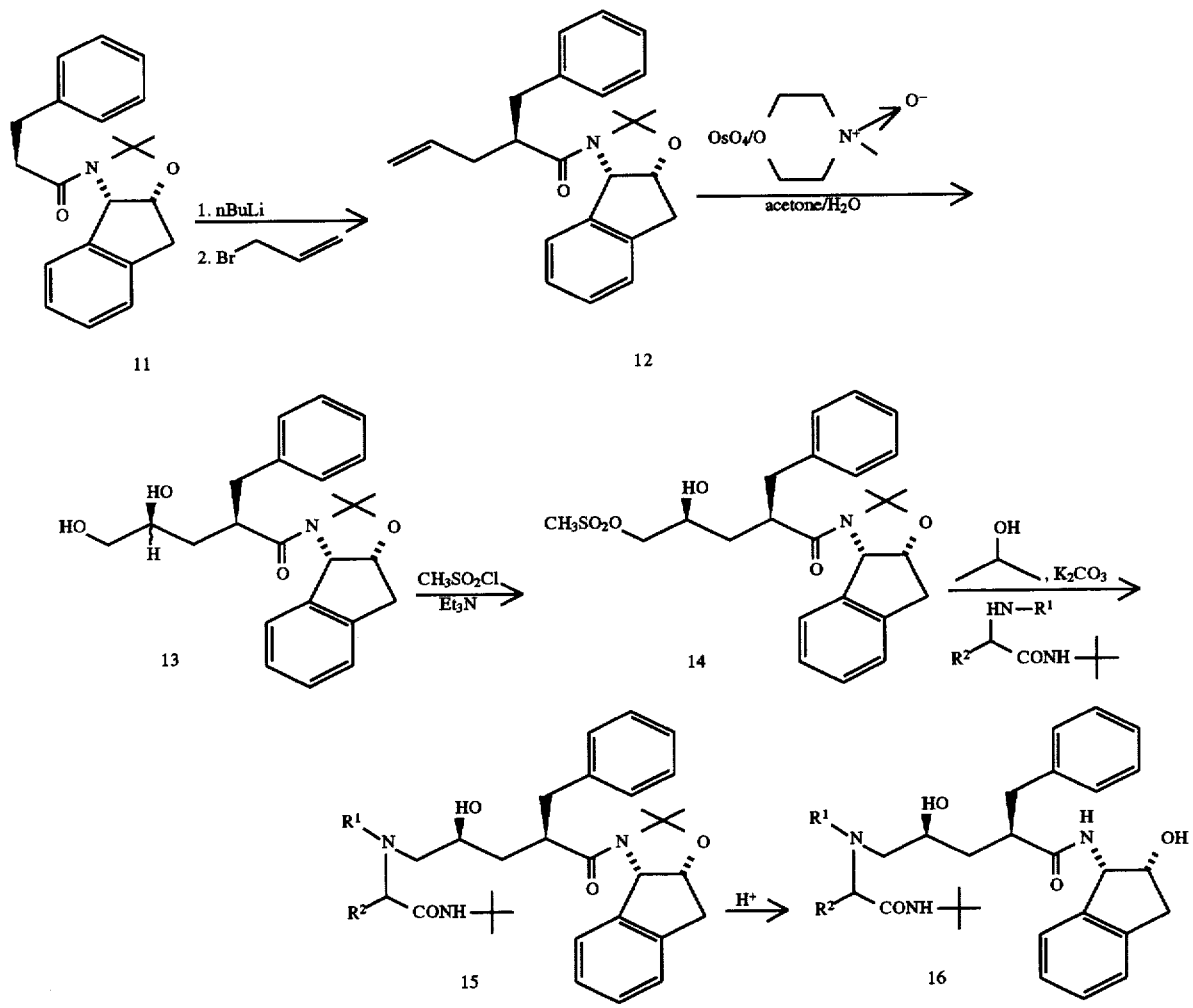

A third method for forming products of general Formula I is shown in Scheme III. Protection of the pyrrolidine —NH— group of compound 17 is carried out with BOC-anhydride and dimethylaminopyridine to give the protected compound 18. Alkylation of 18 is performed by a first step of deprotonation of 18 with a strong base such as lithium-hexamethyldisilamide (LHMDS) or lithium diisopropylamide (LDA) followed by a second step of adding an alkyl halide (such as benzyl bromide) to afford compound 19.

The TBS protecting and BOC protecting group of 19 are removed by treatment with aqueous HF in acetonitrile to give alcohol 20. Mesylation of the primary alcohol of 20 with methanesulfonyl chloride and either triethylamine or pyridine gives mesylate 21 which is heated with an amine in a refluxing alcoholic solvent such as methanol or isopropanol which contains an excess of potassium carbonate to produce an amino pyrrolidinone such as compound 22. The pyrrolidine —NH— group of 22 is reprotected as a BOC group as before and the resultant compound 23 is hydrolized open with a base such as lithium or sodium hydroxide to afford the acid 24. Compound 24 is then coupled to an $NH_2R^{12}$ amine in a standard manner and the BOC is removed with gaseous HCl or trifluoroacetic acid to give the desired product, exemplified by compound 25.

SCHEME III

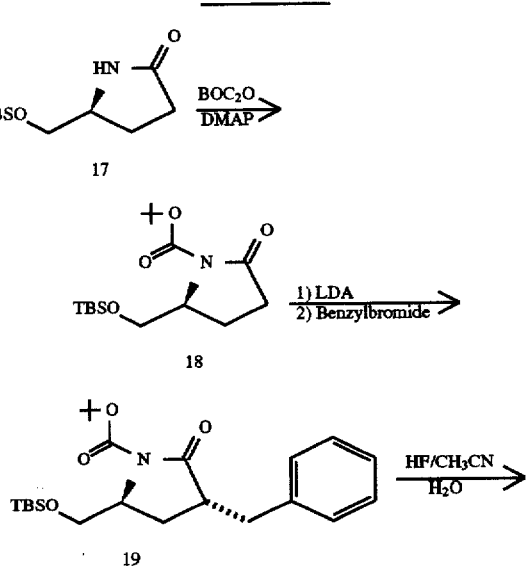

SCHEME III -continued

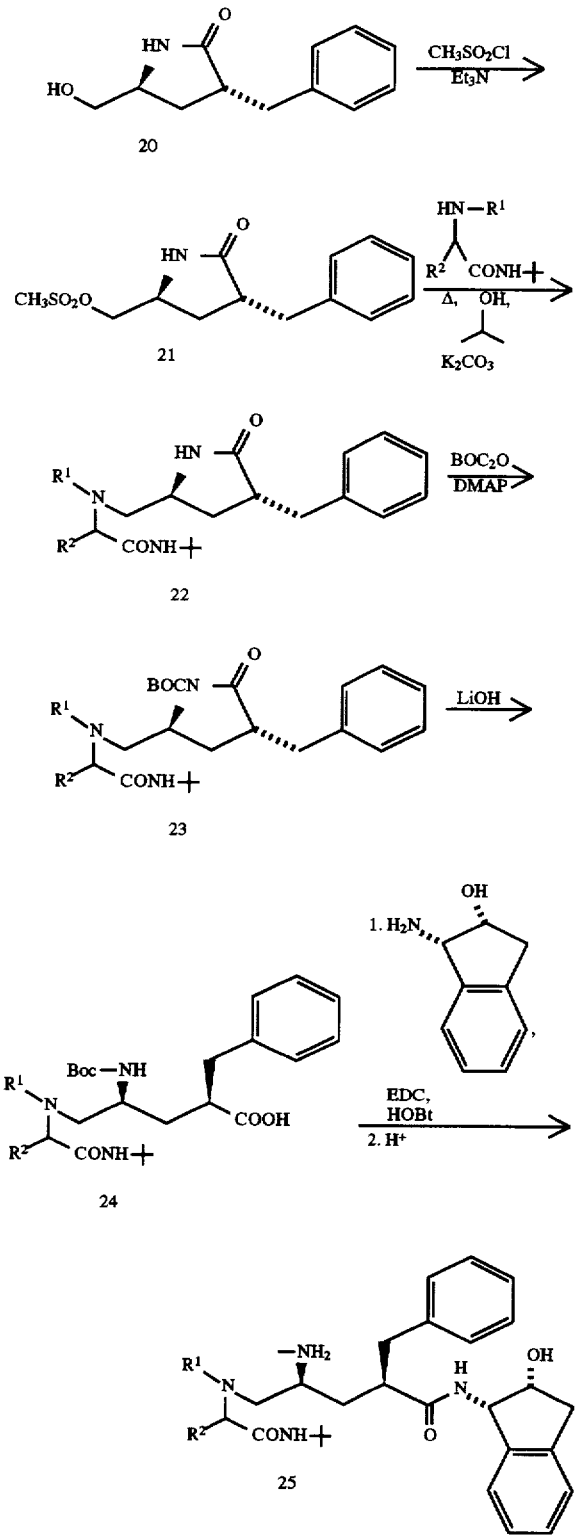

A compound of formula 26

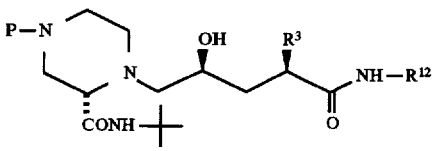

wherein P is a nitrogen protecting group such as —BOC or —CBZ, is preferably prepared according to the method described in Scheme I, preferably employing the 5-trifluoromethanesulfonyloxymethyl analog of lactone 4 therein (see Example 15, Step 1).

Compounds of formula 27

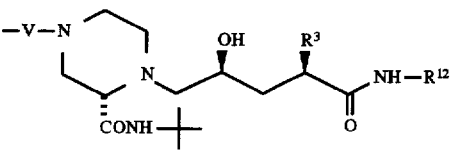

can be obtained by a variety of routes from compound 28

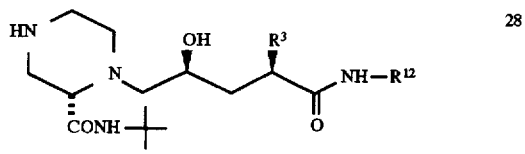

which is obtained after removal of the nitrogen protecting group in 26 using methods well known in the art, e.g., catalytic hydrogenation to remove a CBZ group, or treatment with trimethylsilyltriflate and 2,6-lutidine at about 0° C. in a solvent such as $CH_2Cl_2$ to remove a BOC group.

For example, the 4-position piperazinyl nitrogen of compound 28 can be alkylated with a compound of formula $R^1$—X in a solvent such as DMF in the presence of $Et_3N$ at room temperature, wherein X is —Cl, Br or —I, or a sulfonamide group can be formed by treatment of 28 with a sulfonyl chloride compound of formula $R^1SO_2Cl$ under similar conditions. Also, standard amide coupling techniques can be used to form an amide group at the piperazinyl 4-position. Techniques for these procedures are well known to those skilled in the art. The $R^1$ group of $R^1$—X or $R^1SO_2Cl$ is defined above in the definition of compounds of Formula I wherein $R^1$ is independent from and not joined to $R^2$, except that $R^1$ can not be hydrogen or a group with a free hydroxy substituent, such as —$C_{1-4}$alkyl substituted with hydroxy, with the further exception that $R^1$ can be aryl substituted with a hydroxy group.

The compounds of this invention are also illustrated by Tables I–IV, which follow.

TABLE I
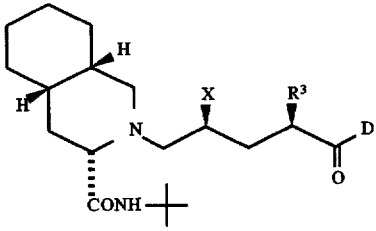
| R³ | X | D |
|---|---|---|
| —CH₂—Ph | —OH | 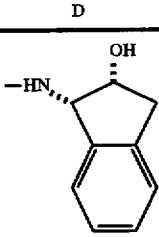 |
| —CH₂—Ph | —OH | 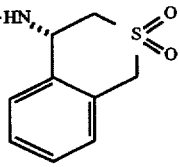 |
| —CH₂—Ph | —OH | 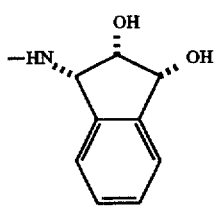 |
| —CH₂—Ph | —OH | 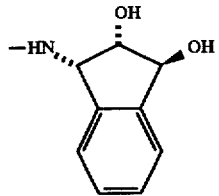 |
| —CH₂—Ph | —OH | 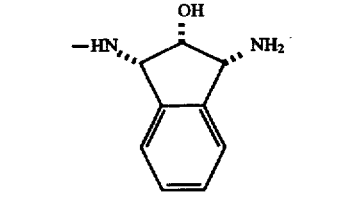 |
| —CH₂—Ph | —OH | 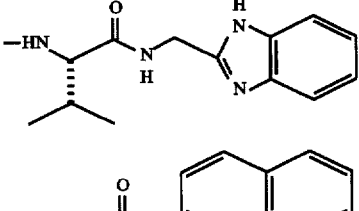 |
| —CH₂—Ph | —OH |  |

TABLE I-continued
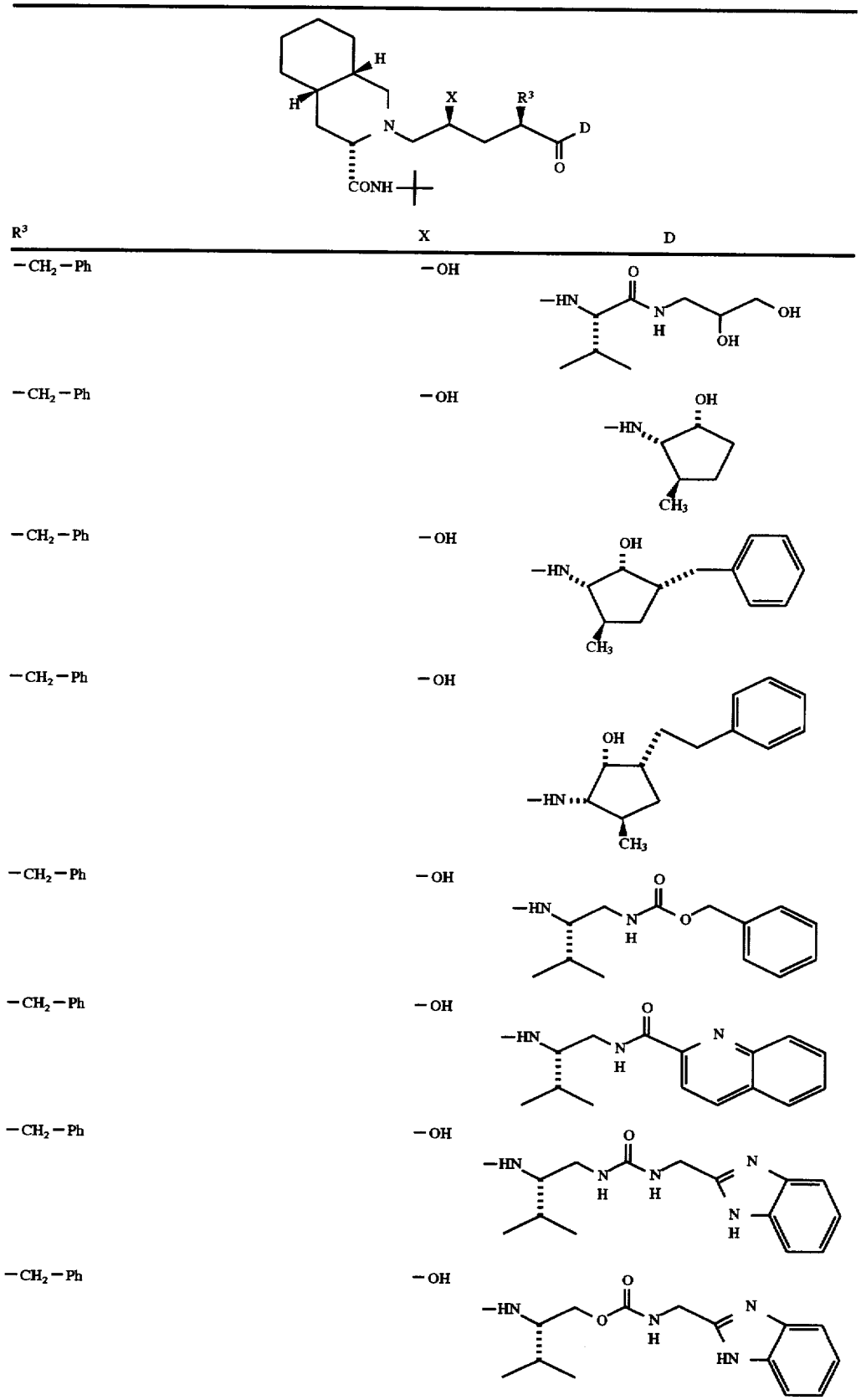

TABLE I-continued

[Structure: decahydroisoquinoline core with N-CH2-CHX-CH(R³)-C(=O)-D substituent and CONH-tBu group]

| R³ | X | D |
|---|---|---|
| —CH₂—Ph | —OH | 4-amino-isothiochroman (NH attached at 4-position of isothiochroman) |
| —CH₂—Ph | —NH₂ | 1-amino-2-hydroxy-indane |
| —CH₂—Ph | —OH | 4-amino-3-hydroxy-chroman |
| —CH₂—Ph | —OH | 4-amino-3-hydroxy-thiochroman |
| —CH₂—Ph | NH₂ | 1-amino-2-hydroxy-tetrahydronaphthalene |
| —CH₂—Ph | —OH | 4-amino-isothiochroman S-oxide |
| —CH₂—Ph | —OH | 1-amino-isothiochroman S,S-dioxide |
| —CH₂—Ph | —OH | 4-amino-thiochroman |

TABLE I-continued

| R³ | X | D |
|---|---|---|
| —CH₃—C₆H₄—CH₃ (p-xylyl) | —OH | 1-amino-2-hydroxy indane (NHMe, OH) |
| —CH₂—C₆H₄—OH | —OH | 1-amino-2-hydroxy indane (NHMe, OH) |
| —CH₂—C₆H₄—OH | —OH | 1-amino-2,3-dihydroxy indane (NHMe, OH, OH) |
| —CH₂—C₆H₄—OH | —NH₂ | 1-amino-2-hydroxy indane (NHMe, OH) |
| —CH₂—C₆H₄—OH | —NH₂ | 1-amino-2,3-dihydroxy indane (NHMe, OH, OH) |
| —CH₂—C₆H₅ | —OH | —IleNH—CH₂—C₆H₅ |
| —CH₂—C₆H₅ | —OH | —IleNH—CH₂—C(=N-benzimidazole) |
| —CH₂—C₆H₅ | —NH₂ | —IleNH—CH₂—C(=N-benzimidazole) |
| —CH₂—C₆H₄—O—CH₂CH₂—N(morpholine) | —OH | —IleNH—CH₂—C(=N-benzimidazole) |

TABLE I-continued
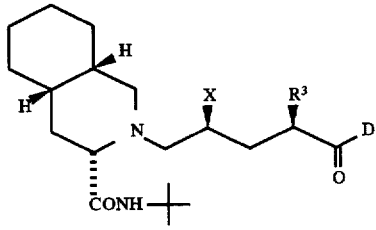
| R³ | X | D |
|---|---|---|
| 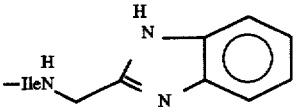 | —OH | 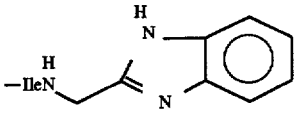 |
| 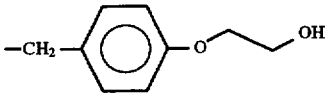 | —NH₂ | 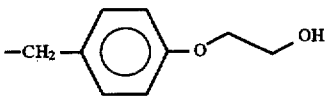 |
| 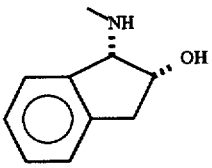 | —OH | 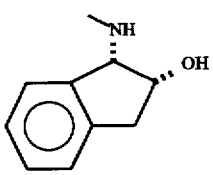 |
| 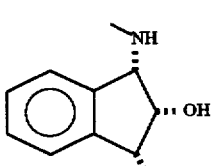 | —OH | 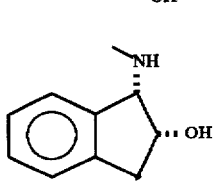 |
| —CH₂—⟨morpholinoethoxyphenyl⟩ | —OH | ⟨methylamino-hydroxyindane⟩ |
| —CH₂—⟨morpholinoethoxyphenyl⟩ | —NH₂ | ⟨methylamino-hydroxyindane⟩ |
| —CH₂—⟨morpholinoethoxyphenyl⟩ | —OH | ⟨methylamino-dihydroxyindane⟩ |
| —CH₂—⟨morpholinoethoxyphenyl⟩ | —OH | ⟨methylamino-hydroxy-aminoindane⟩ |

TABLE I-continued

| R³ | X | D |
|---|---|---|
| -CH₂-C₆H₄-O-CH₂CH₂-N(morpholine) | -NH₂ | indane with NH, OH, NH₂ |
| -CH₂-C₆H₄-O-CH₂CH₂-OH | -OH | indane with NH, OH |
| -CH₂-C₆H₄-O-CH₂CH₂-OH | -OH | indane with NH, OH, NH₂ |
| -CH₂-C₆H₄-O-CH₂CH₂-OH | -NH₂ | indane with NH, OH |
| -CH₂-C₆H₄-O-CH₂CH₂-OH | -NH₂ | indane with NH, OH, NH₂ |
| -CH₂-C₆H₄-O-CH₂CH₂-OH | -OH | isothiochroman S-oxide with NH |
| -CH₂CH=CH-Ph | -OH | indane with HN, OH |
| -CH₂CH=CH-Ph | -OH | isothiochroman S-oxide with HN |

TABLE I-continued
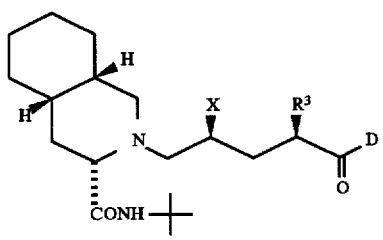
| R³ | X | D |
|---|---|---|
| 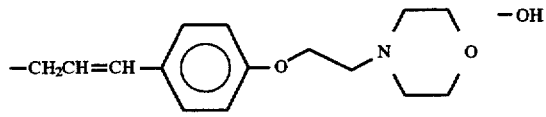 | —OH |  |
| 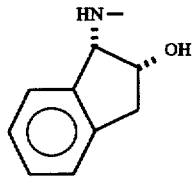 | —OH | 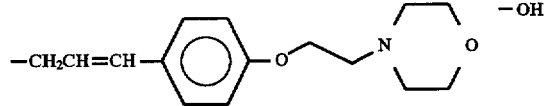 |
TABLE II
| A | X | D |
|---|---|---|
| 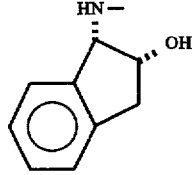 | —OH | 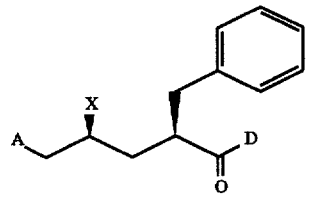 |
| 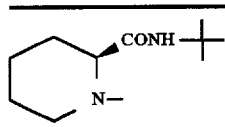 | —OH |  |
| 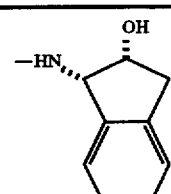 | —NH₂ | 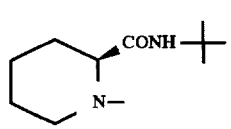 |

TABLE II-continued
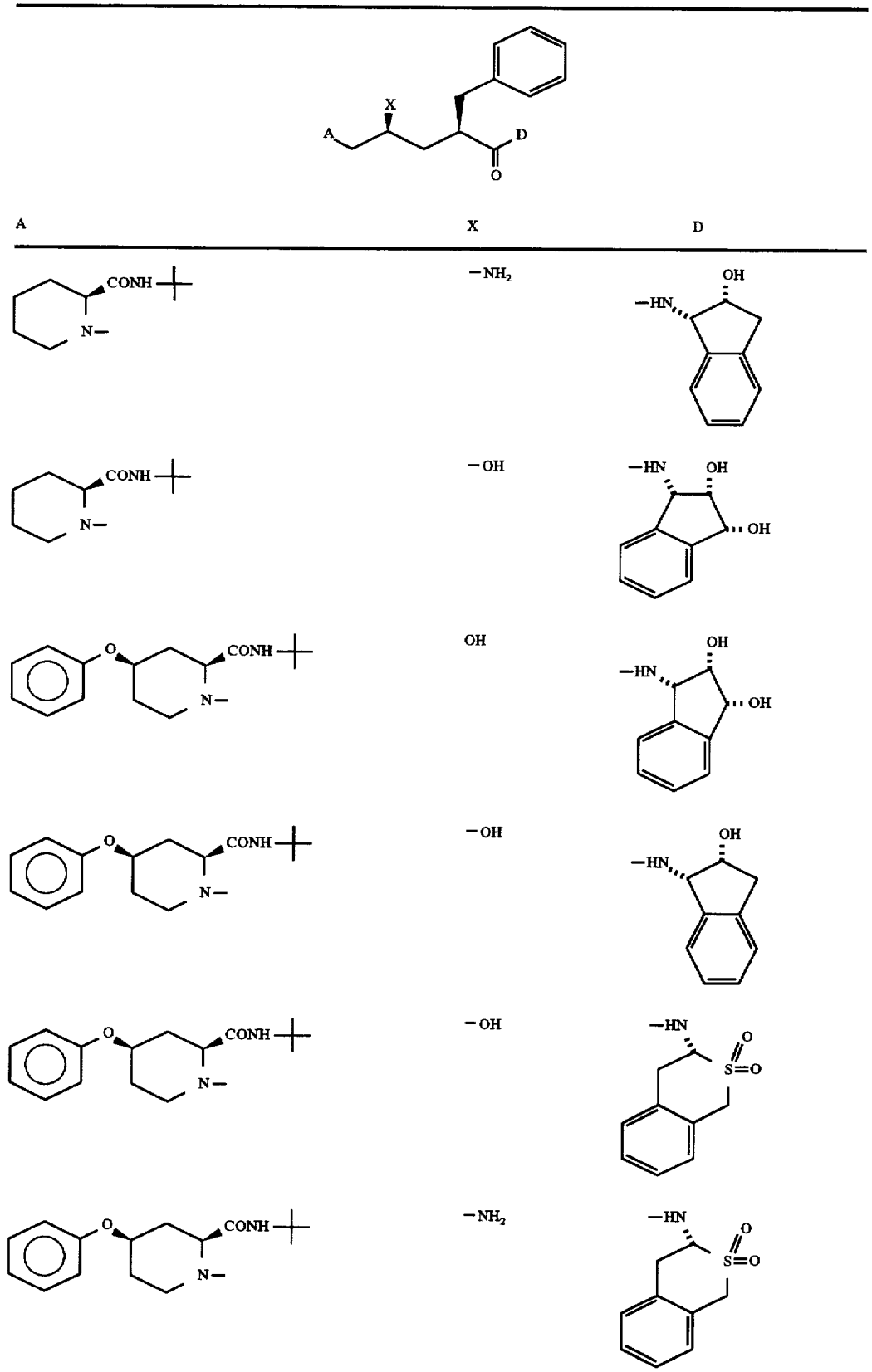

TABLE II-continued
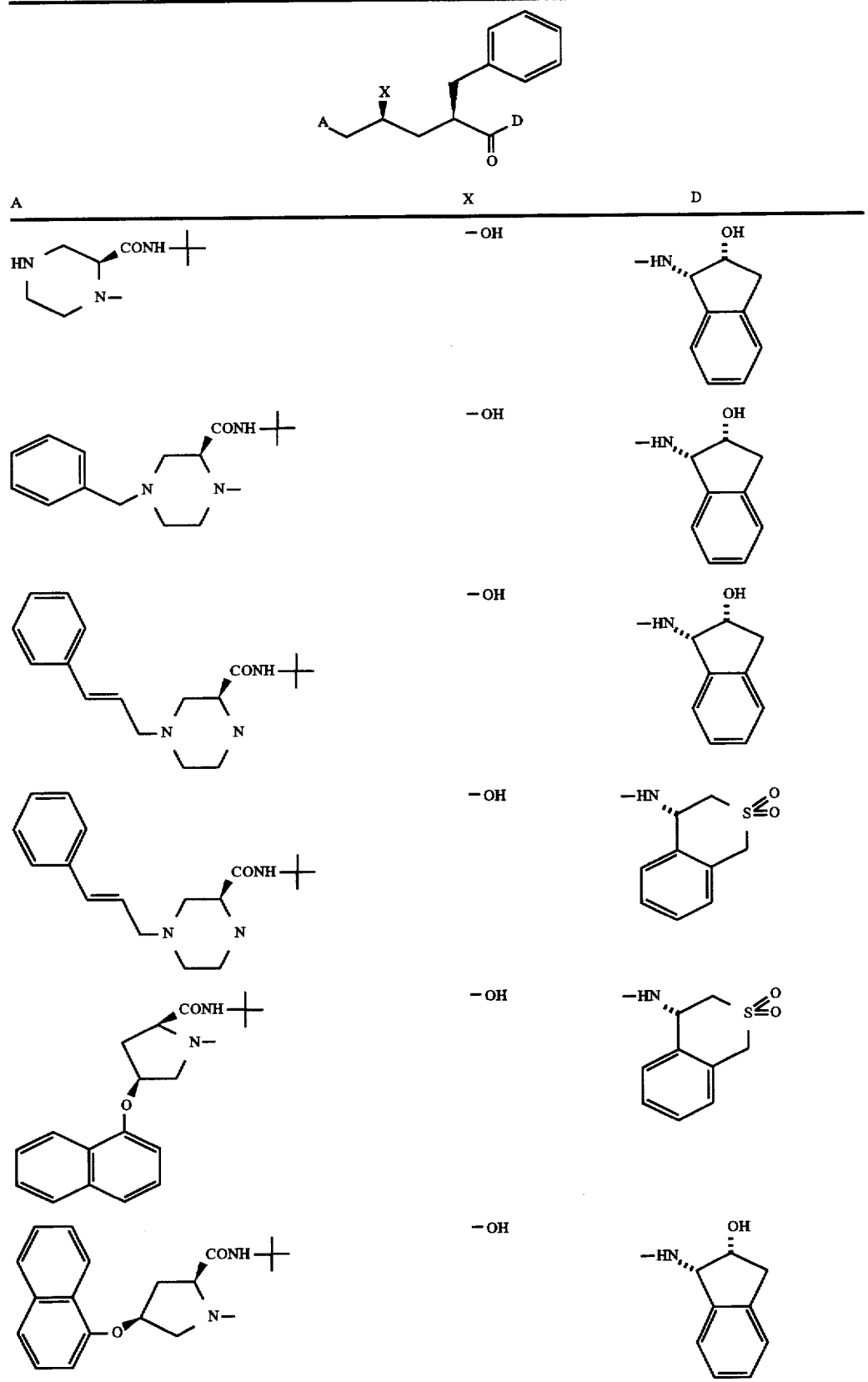

TABLE II-continued
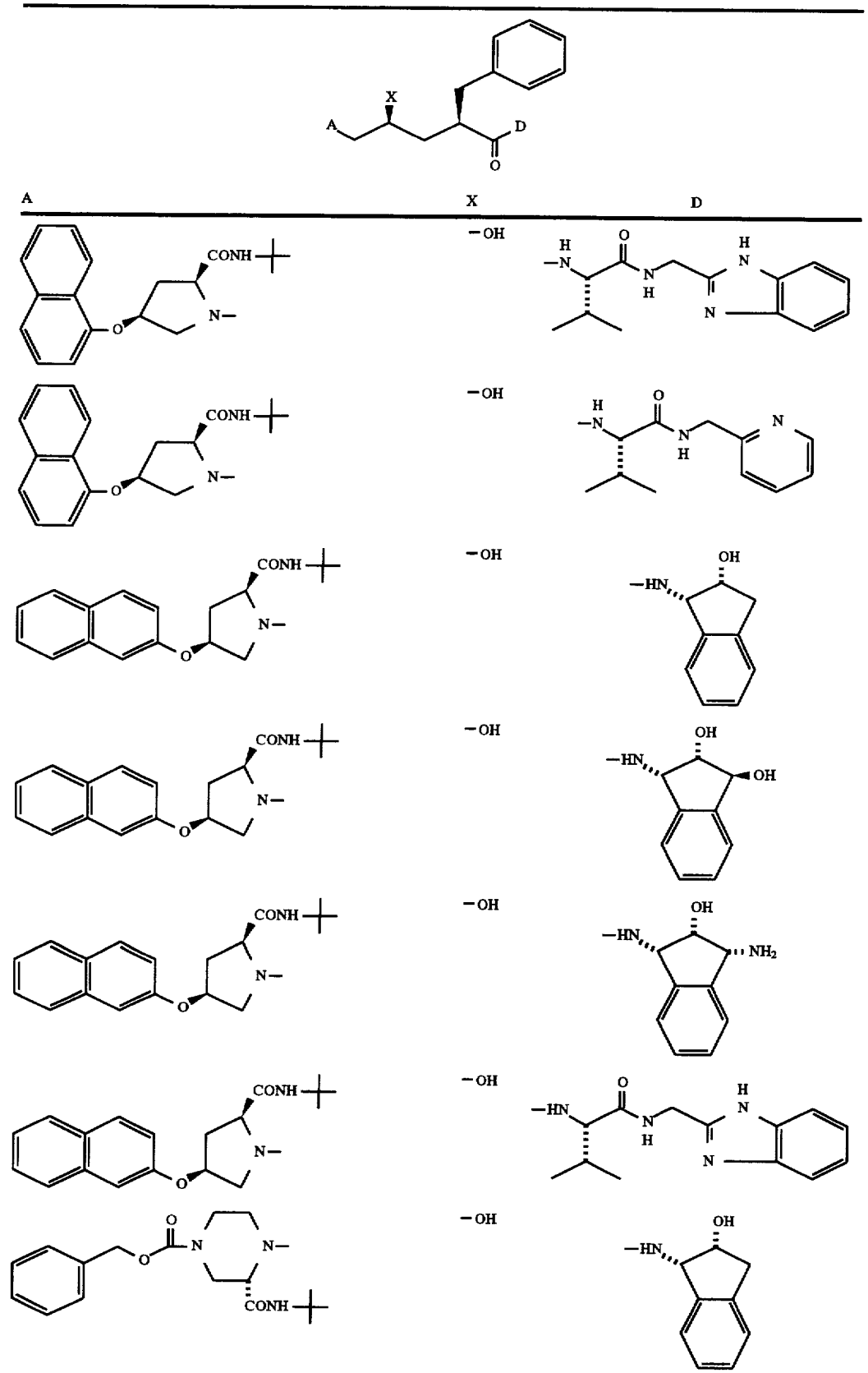

TABLE II-continued
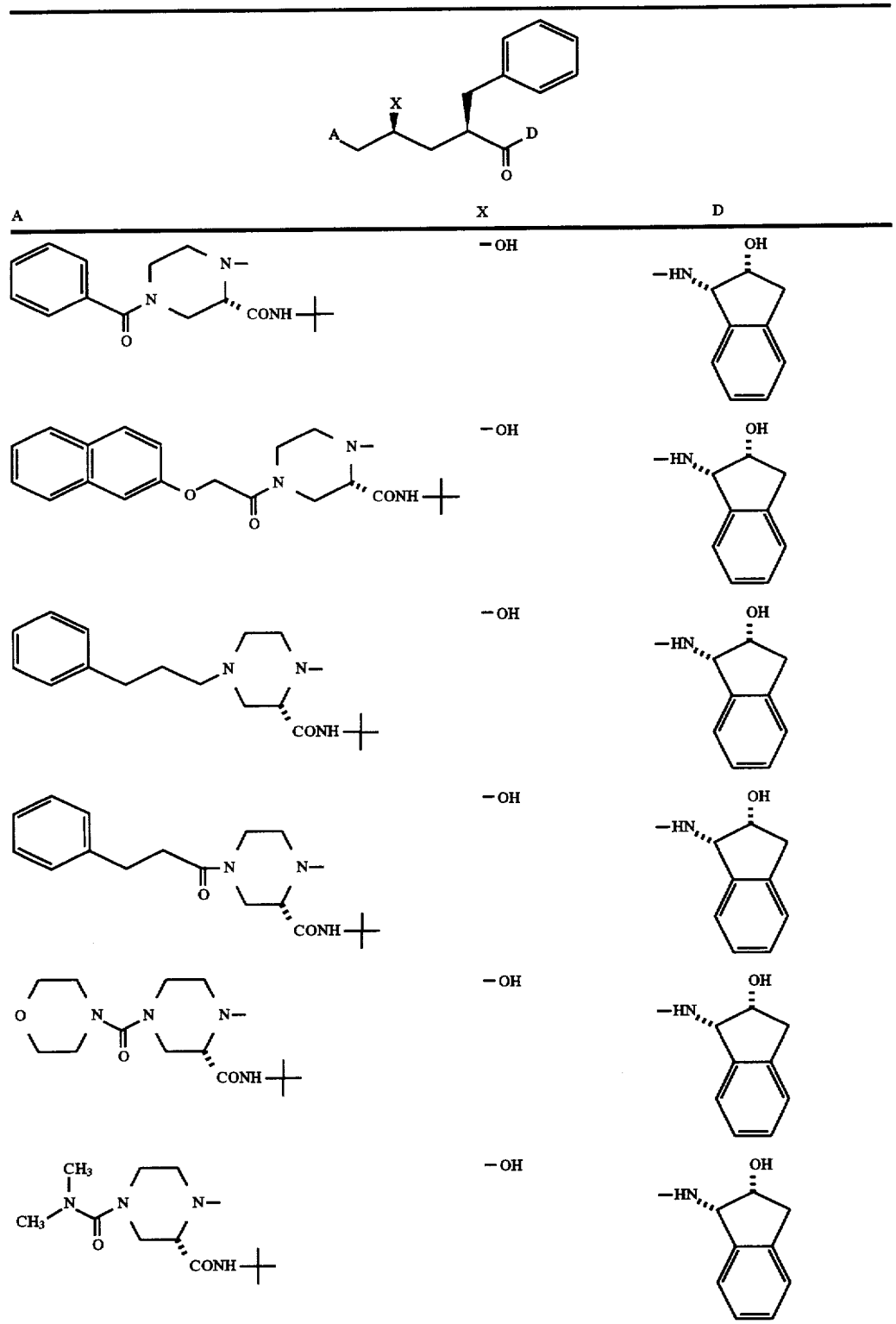

TABLE III

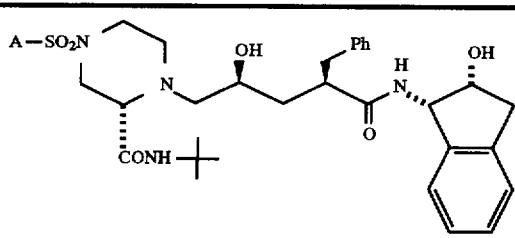

| A |
|---|
| 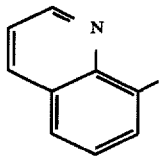 |
| CH₃— |
| 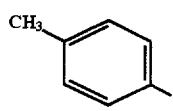 |
| 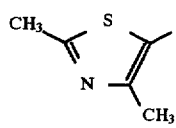 |
| 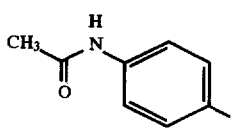 |
| 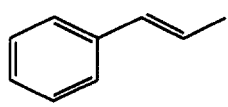 |
| CH₃CH₂CH₂CH₂—<br>(CH₃)₂CH— |
| 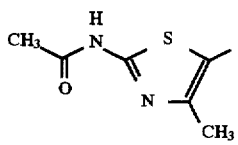 |
| 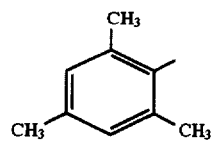 |
| 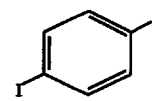 |
| 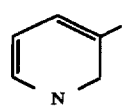 |

TABLE IIIA

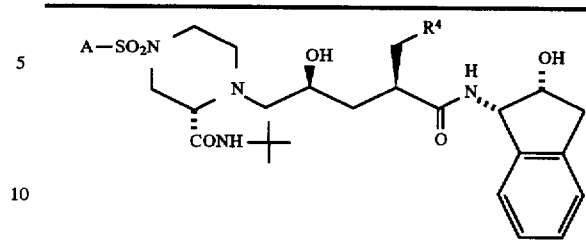

| A | R⁴ |
|---|---|
| 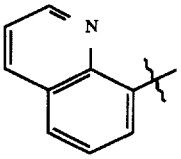 | 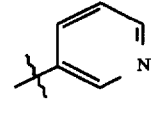 |

TABLE IV

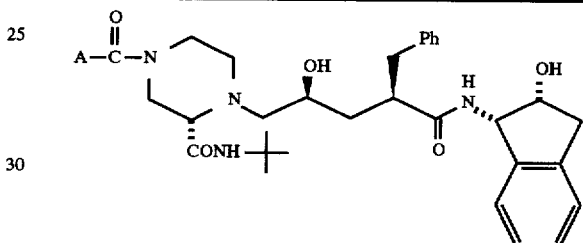

| A |
|---|
| 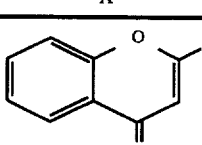 |
| 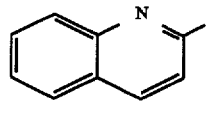 |
| (CH₃)₃C—O— |
| 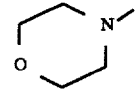 |
| Ph—CH₂CH₂— |

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

The compounds of the present invention are useful in the inhibition of HIV protease the prevention or treatment of infection by the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As mediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known an, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 1.0 to 50 milligrams of the compound per kilogram of body weight from one to four times per day. In one preferred regimen, dosages of 100–400 mg every six hours are administered orally to each patient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drag combination, the severity of the particular condition, and the host undergoing therapy.

The present invention is also directed to combinations of the HIV protease inhibitory compounds with one or more agents useful in the treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

TABLE C

| Drug Name | Manufacturer | Indication |
|---|---|---|
| ANTIVIRALS | | |
| AL-721 | Ethigen (Los Angeles, CA) | ARC, PGL HIV positive, AIDS |
| Recombinant Human Interferon Beta | Triton Biosciences (Almeda, CA) | AIDS, Kaposi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxythymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. Roseville, MN, marketer) | HIV inhibitor |
| Peptide T Octapeptide Sequence | Peninsula Labs (Belmont, CA) | AIDS |
| Zidovudine; AZT AIDS, adv, ARC | Burroughs Wellcome (Rsch. Triangle Park, NC) | AIDS, adv, ARC pediatric ADS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | ADS, ARC, HIV positive asymptomatic |
| Virazole Ribavirin | Viratek/ICN (Costa Mesa, CA) | asymptomatic HIV positive, LAS, ARC |

TABLE C-continued

| Drug Name | Manufacturer | Indication |
|---|---|---|
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption column | Advanced Biotherapy Concepts (Rockville, MD) | AIDS, ARC |
| L-697,661 | Merck Rahway, NJ) | AIDS, ARC, asymptomatic HIV positive, also in combination with AZT. |
| L-696,229 | Merck Rahway, NJ) | AIDS, ARC, asymptomatic HIV positive, also in combination with AZT. |
| IMMUNO-MODULATORS | | |
| AS-101 | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also anti-virals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Sommerville, NJ) Immunex (Seattle, WA) | AIDS |
| Granulocyte Macrophage Colony Stimulating Factor | Schering-Plough (Madison, NJ) | AIDS |
| HIV Core Particle Immunostimulant | Rorer (Ft. Washington, PA) | AIDS, in combination w/AZT seropositive HIV |
| IL-2 Interleukin-2 | Cetus (Emeryville, CA) | AIDS, in combination w/AZT |
| IL-2 Interleukin-2 | Hoffman-La Roche Nutley, NJ) Immunex | AIDS, ARC, HIV, in combination w/AZT |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma w/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |

TABLE C-continued

| Drug Name | Manufacturer | Indication |
|---|---|---|
| Granulocyte Colony Stimulating Factor | Amgen (Thousand Oaks, CA) | AIDS, in combination w/AZT |
| rCD4 Recombinant Soluble Human CD4 | Genentech (S. San Francisco, CA) | AIDS, ARC |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche Nutley, NJ) | Kaposi's sarcoma AIDS, ARC, in combination w/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Fluconazole | Pfizer New York, NY) | cryptococcal meningitis, candidiasis |
| Pastille Nystatin Pastille | Squibb Corp. (Princeton, NJ) | prevention of oral candidiasis |
| Ornidyl Eflornithine | Merrell Dow (Cincinnati, OH) | PCP |
| Pentamidine Isethionate (IM & IV) Trimethoprim Trimethoprim/sulfa | LyphoMed (Rosemont, IL) | PCP treatment antibacterial antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Certain compounds of Table S are the following: L-697, 661 or '661' is 3-([4,7-dichloro-1,3-benzoxazol-2-yl) methyl]-amino)-5-ethyl-6-methylpyridin-2(1H)-one; L-696, 229 is 3-[2-(1,3-benzoxazol-2-yl)-ethyl]-5-ethyl-6-methyl-pyridin-2(1H)-one. The synthesis of L-697,661 and L-696, 229 is described in EPO 484071, and EPO 462800, both herein incorporated by reference. The synthesis of ddC, ddI and AZT are also described in EPO 484071.

Preferred combinations are simultaneous or alternating treatments of an inhibitor of HIV protease and a non-nucleoside inhibitor of HIV reverse transcriptase. An optional third component in the combination is a nucleoside inhibitor of HIV reverse transcriptase, such as AZT, ddC or ddI. A preferred inhibitor of HIV protease is L-735,524 (Compound J). Preferred non-nucleoside inhibitors of HIV reverse include L-697,661. These combinations may have synergistic effects on limiting the spread of HIV. Preferred combinations include the following (1) L-735,524, with L-697,661, and, optionally, AZT or ddI or ddC; (2) L-735, 524, and any of AZT or ddI or ddC.

Assay for Inhibition of Microbial Expressed HIV Protease

Inhibition studies of the reaction of the protease expressed in Eschericia coli with a peptide substrate [Val-Ser-Gln-Asn-(betanapthyl)Ala-Pro-Ile-Val, 0.5 mg/mL at the time the reaction is initiated] were in 50 mM Na acetate, pH 5.5, at 30° C. for 1 hour. Various concentrations of inhibitor in 1.0 µl DMSO were added to 25 µl of the peptide solution in water. The reaction is initiated by the addition of 15 µl of 0.33 nM protease (0.11 ng) in a solution of 0.133M Na acetate pH 5.5 and 0.1% bovine serum albumin. The reaction was quenched with 160 µl of 5% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. The products of synthesis in Examples 1-7 inclusive showed $IC_{50}$ values in the range of 1-100 nM. Compounds A, B and J showed $IC_{50}$ values of between about 0.3 and about 6 nM.

INHIBITION OF VIRUS SPREAD

A. Preparation of HIV-infected MT-4 cell. Suspension.

MT cells were infected at Day 0 at a concentration of 250,000 per ml with a 1:1000 dilution of HIV-1 strain IIIb stock (final 125 pg p24/ml; sufficient to yield≤1% infected cells on day 1 and 25-100% on day 4). Cells were infected and grown in the following medium: RPMI 1640 (Whittaker BioProducts), 10% inactivated fetal bovine serum, 4 mM glutamine (Gibco Labs) and 1:100 Penicillin-Streptomycin (Gibco Labs).

The mixture was incubated overnight at 37° C. in 5% $CO_2$ atmosphere.

B. Treatment with Inhibitors

A matrix of nanomolar range concentrations of the pairwise combinations (see Table S) was prepared. At Day 1, aliquots of 125 µl of inhibitors were added to equal volumes of HIV-infected MT-4 cells (50,000 per well) in a 96-well microtiter cell culture plate. Incubation was continued for 3 days at 37° C. in 5% $CO_2$ atmosphere.

C. Measurement Of Virus Spread

Using a multichannel pipettor, the settled cells were resuspended and 125 µl harvested into a separate microtiter plate. The supernatant was assayed for HIV p24 antigen.

The concentration of HIV p24 antigen was measured by an enzyme immunoassay, described as follows. Aliquots of p24 antigen to be measured were added to microwells coated with a monoclonal antibody specific for HIV core antigen. The microwells were washed at this point, and at other appropriate steps that follow. Biotinylated HIV-specific antibody was then added, followed by conjugated strepavidin-horseradish peroxidase. A color reaction occurs from the added hydrogen peroxide and tetramethylbenzidine substrate. Color intensity s is proportional to the concentration of HIV p24 antigen.

Calculation of Degree of Synergy

Pairwise combinations of inhibitors (see Table 5) were found to exhibit markedly enhanced inhibition of virus spread, in comparison to each inhibitor alone, or in comparison to merely additive inhibition of each inhibitor. Thus, for example, the pairwise combination of 524 and AZT was found to exhibit markedly enhanced inhibition of virus spread, in comparison to 524 alone or AZT, or in comparison to the sum of 524 inhibition and AZT inhibition.

This data was processed as follows: fractional inhibitory concentration ratios (FIC) were calculated according to Elion, et al. *J. Biol. Chem.*, 208, 477 (1954). The minimum sum of FICS, which is the maximum synergy, was determined for various pairwise combinations. See Table S. These results indicate substantial synergy in the inhibition of virus spread. The smaller the number, the greater the synergy.

TABLE S

| Pairwise Combinations* | Maximum Synergy |
| --- | --- |
| 524 + ddI | 0.7 |
| 524 + AZT | 0.7 |
| 524 + 661 | |

524 is L-735,524 (Compound J). Other compounds are also defined in Table C above.

EXAMPLE 1

Preparation of N-(2(R)-hydroxy-1(S)-indanyl)-2(R)-phenylmethyl-4(S)-hydroxy-5-(1-(N'-(t-butyl)-4(S)-phenoxyprolineamide)yl)-pentaneamide Step 1

Preparation of N-(2(R)-hydroxy-1(S)-indanyl)-3-phenylpropaneamide

To a cold (0° C.) solution of methylene chloride (30 ml) containing 2(R)-hydroxy-1(S)-aminoindane (750 mg, 5.0 mmol) and triethylamine (606 mg, 6.0 mmol) was added a solution of hydrocinnamoyl chloride (843 mg, 5.0 mmol) in 5 ml of methylene chloride. After 2 hr the reaction was poured into a separatory funnel containing 50 ml of methylene chloride and washed with 10% citric acid solution (2×30 ml). The organic layer was dried, filtered and concentrated to afford a white solid.

Step 2

Preparation of N-(2(R)-hydroxy-1(S)-indan-N,O-isopropylidene-yl)-3-phenyl-propaneamide The crude white solid from Step 1 above was dissolved in 50 ml of methylene chloride and 5 ml of dimethoxypropane was added followed by the addition of 100 mg of p-toluenesulfonic acid. The reaction was stirred at room temperature for 18 hr and then poured into a separatory funnel and washed with saturated $NaHCO_3$ solution (2×30 ml). The organic layer was dried, filtered and concentrated to afford an oil which was chromatographed ($SiO_2$, 40% EtOAc/Hexane) to give an oil which eventually crystallized.

Step 3

Preparation of N-(2(R)-hydroxy-1(S)-indan-N,O-isopropylidene-yl)-2(S)-phenylmethylpent-4-eneamide To a solution of N-(2(R)-hydroxy-1(S)-indan-N,O-isopropylidene-yl)-3-phenyl-propaneamide (1.03 gm, 2.9 mmol) in 20 ml of THF cooled to −78° C. was added n-BuLi (2.5M, 1.40 ml, 3.5 mmol). After 20 min, allyl bromide (0.48 gm, 3.9 mmol) was added, the reaction was stirred at −78° C. for 1 hr and then 10 ml of saturated $NH_4Cl$ solution was added to quench the reaction. The reaction was diluted with 50 ml of water, extracted with ethyl acetate (2×50 ml), the organic phase was washed with saturated NaCl solution (50 ml), dried filtered and concentrated to afford the crude product. The crude product was purified on silica gel to afford the title compound.

Step 4
Preparation of N-(2(R)-hydroxy-1(S)-indan-N,O-isopropylidene-yl)-2(S)-phenylmethyl-(4(RS),5-dihydroxy)pentaneamide To 800 mg (2.2 mmol) of N-(2(R)-hydroxy-1(S)-indan-N,O-isopropylidene-yl)-2(S)-phenylmethyl-pent-4-eneamide dissolved in 40 ml of a 9:1 mixture of acetone/water was added 0.8 ml of a 60% solution of N-methylmorpholine-N-oxide in water followed by 4 ml of a 2.5% solution of osmium tetroxide in t-BuOH. After 18 hr, excess solid sodium bisulfate was added, the reaction was stirred for 2 hr and then filtered through a pad of celite. The filtrate was concentrated, diluted with 50 ml of water, extracted with methylene chloride (2×50 ml), the organic phase was dried, filtered and concentrated to give the product as a foam.

Step 5
Preparation of N-(2(R)-hydroxy-1(S)-indan-N,O-isopropylidene-yl)-2(S)-phenylmethyl-4(RS)-hydroxy-5-methanesulfonyloxy-pentaneamide To 200 mg (0.527 mmol) of N-(2(R)-hydroxy-1(S)-indan-N,O-isopropylidene-yl)-2(S)-phenylmethyl-(4(RS),5-dihydroxy)pentaneamide dissolved in 7 ml of methylene chloride at 0° C. was added triethylamine (59 mg, 0.58 mmol), followed by methanesulfonyl chloride (66 mg, 0.579 mmol). After 4 hr the reaction was worked up by washing with 10% citric acid solution (2×50 ml) and the organic phase was dried, filtered and concentrated to afford the monomesylate as a mixture of alcohols.

Step 6
Preparation of N'-t-butyl-N-Boc-4(R)-hydroxy-L-prolineamide

To a solution of N-Boc-4(R)-hydroxyproline (2.00 g) in DMF (20 mL) cooled to 0° C. was added EDC (1.987 g), HOBt (1.401 g), tert butyl amine (1.09 mL) and triethylamine (2.41 mL). After 18 h the reaction mixture was diluted with ethyl acetate (150 mL) and washed with 10% HCl, saturated NaHCO₃, water and brine. The solution was then dried over MgSO₄ and concentrated to afford a white s solid.

Step 7
Preparation of N'-t-butyl-N-Boc-4(S)-phenoxy-L-prolineamide

To a solution of N'-t-butyl-N-Boc-4(R)-hydroxy-L-prolineamide (0.6 g) in THF (5 mL) was added phenol (0.295 g), triphenylphosphine (0.824 g) and then diethylazodicarboxylate (0.495 mL) dropwise. The reaction mixture stirred for 24 h at ambient temperature and was diluted with ethyl acetate (200 mL) and washed with saturated NaHCO₃, water, brine and dried over MgSO₄. Concentration in vacuo afforded a yellow oil which was purified by flash chromatography (elution hexane: EtOAc 1:1, 30 mm column).

Step 8
Preparation of N-t-butyl-4(S)-phenoxy-L-prolineamide trifluoroacetic acid salt To a solution of N'-t-butyl-N-Boc-4(S)-phenoxy-L-prolineamide (0.596 g) in methylene chloride (4 mL) at 0° C. was added trifluoroacetic acid (2 mL). After 30 min the reaction was warmed to room temperature and stirred for two hours. The solvent was removed in vacuo and a slightly yellow oil was obtained.

Step 9
Preparation of N-(2(R)-hydroxy-1(S)-indan-N,O-isopropylidene-yl)-2-(R)-phenylmethyl-4-(S)-hydroxy-5-(1-(N'-(t-butyl)-4(S)-phenoxy-prolineamide)yl)-pentaneamide To a solution of N-t-butyl-4(S)-phenoxy-L-prolineamide trifloroacetic acid salt (0.36 g) and N-(2(R)-hydroxy-1(S)-indan-N,O-isopropylidene-yl)-2(S)-phenylmethyl-4(RS)-hydroxy-5-methanesulfonyloxy-pentaneamide (0.226 g) in 3 mL of isopropanol was added potassium carbonate (0.441 g) and the reaction was warmed to 80° C. After 18 h the reaction was cooled to room temperature, filtered through celite which was washed with further portions of EtOAc. The filtrate was concentrated, the residue was dissolved in EtOAc (100 mL) and washed with water, brine and dried over MgSO₄. The solvent was removed in vacuo and the resulting oil was purified by flash chromatography to afford the product as a mixture of diastereomers.

Step 10
Prep of N-(2(R)-hydroxy-1(S)-indanyl)-2-(R)-phenylmethyl-4-(S)-hydroxy-5-(1-(N'-t-butyl-4(S)-phenoxy-prolineamid)yl)pentaneamide To a solution of N-(2(R)-hydroxy-1(S)-indan-N,O-isopropylidene-yl)-2-(R)-phenylmethyl-4-(S)-hydroxy-5-(1-(N'-(t-butyl)-4(S)-phenoxyprolineamide)-yl)-pentaneamide (0.13 g) in MeOH (5 mL) was added camphorsulfonic acid (CSA) (0.070 g) at ambient temperature. After 5 hours more CSA (0.025 g) was added and the reaction was stirred for total of 18 hours. The reaction was quenched with saturated NaHCO₃ (5 mL) and the solvent was removed to a volume of 4 mL. The aqueous layer was thoroughly extracted with EtOAc and the organic layer was washed with water, brine and dried. After removal of the solvent in vacuo the resulting oil was purified via flash chromatography to provide the title compound as a white foam. The foam was dissolved in EtOAc:hexanes and the mother liquor was decanted away from the oil. The oil was then dried in a high vacuum desiccator to afford a white foam.

EXAMPLE 2

Preparation of N-(2(R)-hydroxy-1(S)-indanyl)-2(R)-phenylmethyl-4(S)-hydroxy-5-(1-(N'-t-butyl-4(S)-2-naphthyloxy-prolineamid)yl)-pentaneamide Step 1
Preparation of N-t-butyl-4(S)-2-naphthyloxy-L-prolineamide trifluoroacetic acid salt Following substantially the same procedure for synthesizing N-t-butyl-4(S)-phenoxy-L-prolineamide trifluoroacetic acid salt as outlined in Example 1, Steps 6 through 8, but substituting 2-naphthol for the phenol used therein, the 2-naphthyloxy proline amide was produced.

Step 2
Preparation of N-(2(R)-hydroxy-1(S)-indanyl)-2(R)-phenylmethyl-4(S)-hydroxy-5-(1-(N'-t-butyl -4(S)-2-naphthyloxy-prolineamid)yl)pentaneamide The title compound was produced by following substantially the same procedure outlined in Example 1, Steps 9 and 10, but substituting N-t-butyl-4(S)-2-naphthyloxy-L-prolineamide trifluoroacetic acid salt for the N-t-butyl-4(S)-phenoxy-L-prolineamide trifloroacetic acid salt used in Step 9 therein.

EXAMPLE 3

Preparation of N-(2(R)-hydroxy-1(S)-indanyl)-2(R)-phenylmethyl-4(S)-hydroxy-5-(1-(N'-t-butyl-4(S)-1-naphthyloxy-prolineamid)yl)-pentaneamide Step 1
Preparation of N-t-butyl-4(S)-1-naphthyloxy-L-prolineamide trifluoroacetic acid salt Following substantially the same procedure for synthesizing N-t-butyl-4(S)-phenoxy-L-prolineamide trifluoroacetic acid salt as outlined in Example 1, Steps 6 through 8, but substituting 1-naphthol for the phenol used therein, the 1-naphthyloxy proline amide was produced.

Step 2

Preparation of N-(2(R)-hydroxy-1(S)-indanyl)-2(R)-phenylmethyl-4(S)-hydroxy-5-(1-(N'-t-butyl-4(S)-2-naphthyloxy-prolineamid)yl)pentaneamide The title compound was produced by following the procedure outlined in Example 1, Steps 9 and 10, but substituting N-t-butyl-4(S)-1-naphthyloxy-L-prolineamide trifluoroacetic acid salt for the N-t-butyl-4(S)-phenoxy-L-prolineamide trifluoroacetic acid salt used in Step 9.

EXAMPLE 4

Preparation of N-(2(R)-hydroxy-1(S)-indanyl)-2(R)-phenylmethyl-4(S)-hydroxy-5-(2-(3(S)-N'-(t-butylcarboxamido)-(4aS,8aS)-decahydroisoquinoline)yl) pentaneamide Step 1

Preparation of dihydro-5(S)-((t-butyldiphenylsilyl) oxymethyl)-3(R)phenylmethyl-3(2H)-furanone A solution of lithium diisopropylamide (LDA) was generated by the addition 1.55 ml of n-BuLi (2.5M in hexane) to 0.55 ml (3.9 mmol) of diisopropylamine in 10 ml of THF at −78° C. After 30 minutes a solution of dihydro-5-(S)-((t-butyldiphenylsilyl)-oxymethyl)-3(2H)-furanone (1.38 g, 3.89 mmol) in 5 ml of THF was added. After an additional 30 minutes of stirring, benzyl bromide (0.68 g, 3.9 mmol) was added and stirring was continued for 3 h after which time the reaction was quenched with the addition of a 10% aqueous citric acid solution. The solution was extracted with ethyl acetate (2×50 ml) which was backwashed with brine, dried, filtered and concentrated to afford an oil. The product was purified by chromatography (SiO$_2$, 20% EtOAc/Hexane) to afford the title compound.

Step 2

Preparation of dihydro-5(S)-(hydroxy-methyl)-3(R)-phenylmethyl-3(2H)-furanone

To 5.26 g of dihydro-5(S)-((t-butyldiphenylsilyl) oxymethyl)-3(R)phenylmethyl-3(2H)-furanone in 40 ml of acetonitrile was added 1.34 ml of a 49% aqueous HF solution. After 18 hr at room temperature the reaction was concentrated to dryness and the residue was partitioned between water (50 ml) and ethyl acetate (50 ml). The organic layer was washed with brine, dried filtered and concentrated to afford the product as a tan solid (mp 69°–72° C.).

Step 3

Preparation of dihydro-5(S)-((methane-sulfonyl)oxymethyl)-3(R)phenylmethyl-3(2H)-furanone To a solution of 2.93 g (14 mmol) of dihydro-5(S)-(hydroxymethyl)-3(R)-phenylmethyl-3(2H)-furanone in methylene chloride cooled to 0° C. was added triethylamine (1.98 ml, 15.6 mmol) followed by the addition of methanesulfonyl chloride (1.20 ml, 15.6 mmol). After 1 hour at 0° C., the reaction was poured into 10% aqueous citric acid solution, washed with ethyl acetate (2×100 ml) which was backwashed with water (100 ml), brine (100 ml), dried, filtered and concentrated to give the product as a waxy brown solid.

Step 4

Preparation of dihydro-5(S)-(2-(3(S)-N-(t-butylcarbamoyl)-(4aS,8aS)-(decahydroiso-quinoline)yl)methyl)-3(R)-phenylmethyl-3(2H)-furanone To 70 mg of dihydro-5(S)-((methanesulfonyl)oxymethyl)-3(R)phenylmethyl-3(2H)-furanone (0.25 mmol) in 10 ml of xylene containing 100 mg of potassium carbonate was added 65 mg (0.27 mmol) of N-t-butyl(4aS,8aS)-(decahydroisoquinoline)-3(S)-carboxamide and the reaction was heated to 140° C. After 6 hours, the reaction was cooled, poured into 30 ml of water which was washed with ethyl acetate (2×30 ml). The organic phase was dried, filtered and concentrated to afford a residue which was chromatographed (50/50 EtOAc/Hexane) to give the product.

Step 5

Preparation of 2(R)-phenylmethyl-4(S)-(t-butyldimethylsilyloxy)-5-(2-(3(S)-N-(t-butylcarbamoyl) (4aS,8aS)-decahydroisoquinoline)yl)pentanoic acid To 130 mg (0.305 mmol) of dihydro-5(S)-(2-(3(S)-N-(t-butylcarbamoyl)-(4aS,8aS)-(decahydroisoquinoline)yl) methyl)-3(R)-phenylmethyl-3-(2H)furanone in 2 ml of DME was added 1 ml lithium hydroxide solution. After 4 hours at room temperature, the reaction was concentrated to dryness and azeotroped with toluene (3×) to remove excess water. The residue was dissolved in 5 ml of DMF and 414 mg (6.10 mmol) of imidazole and 465 mg (3.05 mmol) of t-butyldimethylsilyl chloride was added. After two days at room temperature, 1 ml of methanol was added to the reaction and after 1 hour the solution was evaporated to dryness. The residue was partitioned between saturated NH$_4$Cl solution (aq) and washed with ethyl acetate which was dried, filtered and concentrated to give an oil which was a mixture of product and the furanone starting material. This material was carried on crude into the next reaction.

Step 6

Preparation of N-(2(R)-hydroxy-1(S)-indanyl)-2(R)-phenylmethyl-4(S)-(t-butyldimethyl-silyloxy-5-(2-(3(S)-N'-(t-butylcarbamoyl)-(4aS,8aS)-decahydroisoquinoline)yl) pentaneamide The crude product of Step 5, above, was dissolved in 3 ml of DMF along with 47 mg (0.246 mmol) of EDC, 33 mg (0.246 mmol) of HOBT and 37 mg of 2(R)-hydroxy-1(S)-aminoindane. The pH of the solution was adjusted to 8.5–9.0 with triethylamine and after 18 hours it was worked up by concentrating to dryness, dissolving the residue in 10% aq. citric acid solution and washing the aqueous layer with ethyl acetate. The organic layer was dried, filtered and concentrated and the resultant oil was chromatographed (SiO$_2$, 30% EtOAc/Hexane) to yield the title compound.

Step 7

Preparation of N-(2(R)-hydroxy-1(S)-indanyl)2(R)-phenylmethyl-4(S)-hydroxy-5-(2-(3(S)-N'-(t-butylcarbamoyl)-(4aS,8aS)-decahydro-isoquinoline)yl)-pentaneamide The product from Step 6, above, was dissolved in 1 ml of THF and 1 ml of a 1M solution of tetrabutylammonium fluoride in THF was added. After 18 hr at room temperature the reaction was diluted with 20 ml of saturated NaHCO$_3$ solution (aq) and the product was extracted into ethyl acetate which was dried, filtered and concentrated to give a foam. The resultant material was chromatographed on a prep plate (0.5 mm, 5% MeOH/CHCl$_3$) and the title product isolated in the usual manner as a solid with mp 105°–107° C.

EXAMPLE 5

Preparation of N-(2(R)-hydroxy-1(S)-indanyl)-2(R)-phenylmethyl-4(S)-amino-5-(2-(3(S)-N'-(t-butylcarbamoyl) -(4aS,8aS)-decahydroisoquinoline)yl)pentaneamide Step 1

Preparation of 5(S)-((t-butyl-dimethylsilyloxy)methyl)-3(R) -phenylmethyl-N-BOC-2-pyrrolidinone A solution of 5(S)-((t-butyl-dimethylsilyloxy)methyl)-N-BOC-2-pyrrolidinone (400 mg, 1.26 mmol) in 2 ml of THF was added to a precooled (−78° C.) 1M solution of lithium hexamethyldisilazide (1.3 ml) in 5 ml of THF. After 45 min, 0.15 ml of benzyl bromide (1.3 mmol) was added and the stirring was continued. After 5 h the reaction was worked up by pouring into a separatory funnel containing 30 ml of an aqueous 10% citric solution. The aqueous layer was extracted (2×30 ml EtOAc) which was backwashed with brine (50 ml) dried, filtered and concentrated to an oil. The residue was chromatographed (SiO$_2$, 20% EtOAc/Hexane) to afford the product as an oil.

Step 2

Preparation of 5(S)-hydroxymethyl-3(R)-phenylmethyl-2-pyrrolidinone

To 130 mg (0.34 mmol) of 5(S)-((t-butyl-dimethylsilyloxy)methyl)-3(R)-phenylmethyl-N-BOC-2-pyrrolidinone in 5 ml of acetonitrile was added 0.1 ml of a solution of 48% HF in water. After 3 hr at room temperature the reaction was concentrated to dryness and diluted with 30 ml of an aqueous 10% NaHCO$_3$ solution. This was extracted with EtOAc (2×30 ml), dried filtered and concentrated to afford the crude product.

Step 3

Preparation of 5(S)-(methanesulfonyloxy)methyl-3(R)-phenylmethyl-2-pyrrolidinone To a solution of the crude product from Step 2, in 5 ml of methylene chloride cooled to 0° C. was added triethylamine (42 mg, 0.41 mmol) and methanesulfonyl chloride (47 mg, 0.41 mmol). The reaction was slowly allowed to warm to room temperature and was stirred for 18 hr after which time it was diluted with 30 ml of methylene chloride, washed with 30 ml of 10% citric acid solution, dried filtered and concentrated to afford the product as an oil.

Step 4

Preparation of 5(S)-(2-(3(S)-N-(t-butylcarboxamido)-(4aS,8aS)-(decahydroisoquinoline)-yl)-methyl)-3(R)-phenylmethyl-2-pyrrolidinone To a solution of 380 mg (1.34 mmol) of 5(S)-(methanesulfonyloxy)methyl-3(R)-phenylmethyl-2-pyrrolidinone in 20 ml of isopropanol was added 350 mg of potassium carbonate and 360 mg of N-t-butyl-(4aS,8aS)-(decahydroisoquinoline)-3(S)-carboxamide and the reaction was heated to 85° C. After 18 hr the cooled reaction was filtered through celite, evaporated to dryness and the residue was dissolved in water which was extracted with EtOAc (2×50 ml). The organics were dried, filtered and concentrated, and the residue was chromatographed (SiO$_2$, 50/50 EtOAc/Hexane) to afford the product as an oil.

Step 5

Preparation of 5(S)-(2-(3(S)-N'-(t-butylcarboxamido)-(4aS,8aS)-(decahydroisoquinoline)-yl)-methyl)-3(R)-phenylmethyl-N-BOC-2-pyrrolidinone To a solution of the product from Step 4, above, (260 mg, 0.611 mmol) in 10 ml of methylene chloride was added dimethylaminopyridine (74 mg, 0.6 mmol) and 133 mg (0.61 mmol) of BOC-anhydride. After 18 hr at room temperature the reaction was worked up by diluting with 30 ml of methylene chloride and the organics washed with 30 ml of 10% citric acid solution, brine (30 ml) dried, filtered and concentrated to afford an oil. Chromatography (SiO$_2$, 40% EtOAc/Hexane) gave the title compound.

Step 6

Preparation of 5-(2-(3(S)-N'-(t-butylcarbamoyl)-(4aS,8aS)-decahydroisoquinoline)-yl)-4(S)-[(1',1')-(dimethylethoxycarbonyl)-amino]-2(R)-phenylmethyl-pentanoic acid To a solution of the product of Step 5, above, (260 mg, 0.495 mmol) dissolved in 3 ml of dimethoxyethane was added 1.5 ml of a 1M solution of aqueous lithium hydroxide (1.5 mmol). The reaction was worked up after 2 hr by concentrating to dryness, dissolving the residue in saturated aqueous ammonium chloride solution and the aqueous phase was washed with ethyl acetate (2×50 ml) which was dried, filtered and concentrated to afford the crude acid.

Step 7

Preparation of N-(2(R)-hydroxy-1(S)-indanyl)-2(R)-phenylmethyl-4(S)-[(1',1')-(dimethylethoxycarbonyl)-amino]-5-(2-(3(S)-N'-(t-butylcarbamoyl)-(4aS,8aS)-decahydroisoquinoline)yl)pentaneamide To a solution of the product of Step 6, above, (260 mg, 0.49 mmol) in methylene chloride was added EDC (94 mg, 0.49 mmol), HOBT (66 mg, 0.49 mmol), 2(R)-hydroxy-1(S)-aminoindane (73 mg, 0.49 mmol) and the pH of the reaction was adjusted to 8.5–9.0 using triethylamine. After 5 hr at room temperature the reaction was worked up by diluting with 50 ml of methylene chloride and washing the organics with saturated aqueous ammonium chloride solution. The organic phase was dried, filtered and concentrated and the residue was chromatographed to afford the title compound as a foam.

Step 8

Preparation of N-(2(R)-hydroxy-1(S)-indanyl)-2(R)-phenylmethyl-4(S)-hydroxy-5-(2-(3(S)-N'-(t-butylcarbamoyl)-(4aS,8aS)-decahydroisoquinoline)yl) pentaneamide To a solution of the product of Step 7, above, (180 mg, 0.28 mmol) in 5 ml of methylene chloride cooled to 0° C. was added 1 ml of trifluoroacetic acid. After 4 hr the reaction was worked up by concentrating to dryness and the residue was dissolved in 50 ml of methylene chloride and washed with 10% aqueous NaHCO$_3$ solution. The organic layer was dried, filtered and concentrated to give the product as a solid which was chromatographed (SiO$_2$, 7% MeOH/CH$_2$Cl$_2$) to afford the title compound, mp=92°–95° C.

EXAMPLE 6

Preparation of N-(2(R)-hydroxy-1(S)-indanyl)-2(R)-phenylmethyl-4(S)-hydroxy-5-(1-(4-carbobenzyloxy-2-(S)-N'-(t-butylcarbamoyl)-piperazinyl))pentaneamide Employing substantially the same procedure used in Example 1, but substituting N-t-butyl-4-CBZ-piperazine-2(S)-carboxamide for N-t-butyl-4(S)-phenoxy-L-prolineamide used in Step 9 therein, the title compound was obtained.

EXAMPLE 7

Preparation of N"-(N-(2-pyridyl)-valyl)-2(R)-phenylmethyl-4(S)-hydroxy-5-(2-(3(S)-(N'-t-butylcarbamoyl)-(4aS,8aS)-decahydroisoquinoline)yl) pentaneamide Employing substantially the same procedure used in Example 4, but substituting N-2-pyridylvaline for the 2(R)-hydroxy-1(S)aminoindane used in Step 6 therein, the title compound was obtained.

EXAMPLE 8

Preparation of N-(2(R)-hydroxy-1(S)-indanyl)-2(R)-phenylmethyl-4(S)-hydroxy-5-(2(S)-(N'-t-butyl-3-phenyl-propionamide)amino)-pentaneamide Employing substantially the same procedure used in Example 1, but substituting N-t-butyl-phenylalanine amide for the N'-t-butyl-4(S)-phenoxy-L-prolineamide used in Step 9 therein, the title compound is obtained.

EXAMPLE 9

Preparation of N-(4(S)-3,4-dihydro-1H-2,2-dioxobenzothiopyranyl)-2(R)-phenylmethyl-4(S)-hydroxy- 5-(2-(3(S)-N'-(t-butylcarbamoyl)-(4aS,8aS)-decahydroisoquinoline)yl)-pentaneamide Step 1

Preparation of N-(4(S)-3,4-dihydro-1H-benzothiopyranyl)-2(R)-phenylmethyl-4(S)-hydroxy-5-(2-(3(S)-t-butylcarbamoyl)-(4aS,8aS)-decahydroisoquinoline)yl)-pentaneamide Employing substantially the same procedure used in Example 4 but substituting 4(S)-amino-3,4-dihydro-1H-benzothiopyran for the 2(R)-hydroxy-1(S)-aminoindane used in Step 6 therein, the title compound is obtained.

Step 2

Preparation of N-(4(S)-3,4-dihydro-1H-2,2-dioxobenzothiopyranyl)-2(R)-phenylmethyl-4(S)-hydroxy-5-(2-(3(S)-t-butylcarbamoyl)-(4aS,8aS)-decahydroisoquinoline)yl)-pentaneamide The compound from Step 1 above is dissolved in a 1:1 mixture of methanol and water. To this is added 10 eq. of OXONE and the reaction is stirred at room temperature. When the reaction is complete, it is concentrated to dryness, water is added and extracted with ethyl acetate which is dried, filtered and concentrated to give the title compound.

EXAMPLE 10

Preparation of N-(4(S)-3,4-dihydro-1H-2,2-dioxobenzothiopyranyl)-2(R)-phenylmethyl-4(S)-hydroxy-5-(1-(4-carbobenzyloxy-2(S)-N'-(t-butylcarbamoyl)-piperazinyl))pentaneamide Step 1

Preparation of dihydro-5(S)-(1-(4-carbobenzyloxy-2(S)-N'-(t-butylcarbamoyl)piperazinyl)methyl)-3(R)-phenylmethyl-3(2H)-furanone Employing substantially the same procedure used in Example 4, Step 4 but substituting 4-carbobenzyloxy-2(S)-N'-(t-butylcarboxamido)-piperazine for the N'-t-butyl-(4aS,8aS)-(decahydroisoquinoline)-3(S)-carboxamide used therein, the title compound is produced.

Step 2

Preparation of 2(R)-phenylmethyl-4(S)-(t-butyldimethylsilyloxy)-5-(1-(4-carbobenzyloxy-2(S)-N'-(t-butylcarbamoyl)-piperazinyl))-pentanoic acid Employing substantially the same procedure used in Example 4, Step 5 but substituting dihydro-5(S)-(1-(4-carbobenzyloxy-2(S)-N'-(t-butylcarboxamido)-piperazinyl)methyl)-3(R)-phenylmethyl-3(2H)-furanone for the dihydro-5(S)-(2-(3(S)-N'-(t-butylcarboxamido)-(4aS,8aS)-(decahydroisoquinoline)yl)methyl)-3(R)-phenylmethyl-3(2H) furanone used therein, the title compound is produced.

Step 3

Preparation of N-(4(S)-3,4-dihydro-1H-benzothiopyranyl)-2(R)-phenylmethyl-4(S)-(t-butyldimethylsilyloxy)-5-(1-(4-carbobenzyloxy-2(S)-N'-(t-butylcarbamoyl)-piperazinyl))pentaneamide The crude 2(R)-phenylmethyl-4(S)-(t-butyldimethylsilyloxy)-5-(1-(4-carbobenzyloxy-2(S)-N'-(t-butylcarbamoyl)piperazinyl))pentanoic acid is dissolved in 3 ml of DMF along with 1 eq of EDC, 1 eq of HOBT and 1 eq of 4(S)-amino-3,4-dihydro-1H-benzothiopyran. The pH of the solution is adjusted to 8.5–9.0 with triethylamine and after 18 hours it is worked up by concentrating to dryness, dissolving the residue in 10% aq citric acid solution and washing the aqueous layer with ethyl acetate. The organic layer is dried, filtered and concentrated and the resultant residue is chromatographed to yield the title product.

Step 4

Preparation of N-(4(S)-3,4-dihydro-1H-benzothiopyranyl)-2(R)-phenylmethyl-4(S)-hydroxy-5-(1-(4-carbobenzyloxy-2(S)-(t-butylcarbamoyl)-piperazinyl))pentaneamide The product from Step 3 above is dissolved in 1 ml of THF and 1 ml of a 1M solution of tetrabutylammonium fluoride in THF is added. After 18 hr at room temperature the reaction is diluted with 20 ml of saturated NaHCO$_3$ solution (aq) and the product is extracted into ethyl acetate which is dried, filtered and concentrated to give a residue. The residue is chromatographed to afford the product.

Step 5

Preparation of N-(4(S)-3,4-dihydro-1H-2,2-dioxobenzothiopyranyl)-2(R)-phenylmethyl-4(S)-hydroxy-5-(1-(4-carbobenzyloxy-2(S)-N'-(t-butylcarbamoyl)piperazinyl))pentaneamide The compound from Step 4 above is dissolved in a 1:1 mixture of methanol and water. To this is added 10 eq of OXONE and the reaction is stirred at room temperature. When the reaction is complete, it is concentrated to dryness, water is added and extracted with ethyl acetate which is dried, filtered and concentrated to give the title compound.

EXAMPLE 11

Preparation of N-(2(R)-hydroxy-1(S)-indanyl)-2(R)-((4-((2-hydroxy)ethoxy)phenyl)methyl)-4(S)-hydroxy-5-(2-(3-(S)-N'-(t-butylcarbamoyl)-(4aS,8aS)-decahydroisoquinoline)yl) pentaneamide Step 1

Preparation of N-(2(R)-hydroxy-1(S)-indanyl)-2(R)-((4-(2-allyloxy)phenyl)methyl)-4(S)-hydroxy-5-(2-(3(S)-t-butylcarbamoyl)-(4aS,8aS)-decahydroisoquinoline)yl) pentaneamide To a solution of N-(2(R)-hydroxy-1(S)-indanyl)-2(R)-((4-hydroxyphenyl)methyl)-4(S)-hydroxy-5-(2-(3(S)-t-butylcarbamoyl)-(4aS,8aS)-decahydroisoquinoline)yl)-pentaneamide in dioxane is added 6 eq of allyl bromide and 6 eq of cesium carbonate. The reaction is heated to 90° C. When the reaction is complete, the precipitate is filtered off, the dioxane is concentrated to dryness and the residue is diluted with water which is washed with ethyl acetate. The organic phase is dried, filtered and concentrated to afford the product.

Step 2

Preparation of N-(2(R)-hydroxy-1(S)-indanyl)-2(R)-((4-((2-hydroxy)ethoxy)phenyl)methyl)-4(S)-hydroxy-5-(2-(3(S)-N'-(t-butylcarbamoyl)-(4aS,8aS)-decahydroisoquinoline)yl) pentaneamide The product from Step 1 above is dissolved in methanol, 1 eq of p-toluenesulfonic acid is added and the reaction is cooled to −78° C. Excess ozone is bubbled through the reaction until a blue color persists. The flask is purged with nitrogen to remove any ozone and excess sodium borohydride solution is added. The reaction is warmed to room temperature and then saturated NaHCO$_3$ solution is added. The methanol is concentrated off on the rotoevaporator and the aqueous residue is washed with ethyl acetate which is dried, filtered and concentrated to afford the title compound.

EXAMPLE 12

Preparation of N-(2(R)-hydroxy-1(S)-indanyl)-2(R)-((4-((2-hydroxy)ethoxy)phenyl)methyl)-4(S)-hydroxy-5-(1-(4-carbobenzyloxy-2(S)-N'-(t-butylcarbamoyl)piperazinyl)) pentaneamide Employing substantially the same procedure used in Example 11 but substituting N-(2(R)-hydroxy-1(S)-indanyl)-2(R)-((4-hydroxyphenyl)methyl)-4(S)-hydroxy-5-(1-(4-carbobenzyloxy-2(S)-(t-butylcarbamoyl)-piperazinyl)-pentaneamide for the N-(2(R)-hydroxy-1(S)-indanyl)-2(R)-((4-hydroxyphenyl)methyl)-4(S)-hydroxy-5-(2-(3(S)-t-

EXAMPLE 13

Preparation of N-(2(R)-hydroxy-1(S)-indanyl)-2(R)-((4-(2-(4-morpholinyl)ethoxy)phenyl)methyl)-4(S)-hydroxy-5-(2-(3(S)-N'-(t-butylcarbamoyl)-(4aS,8aS)-decahydroisoquinoline)yl)pentaneamide To a solution of N-(2(R)-hydroxy-1(S)-indanyl)-2(R)-((4-hydroxyphenyl)methyl)-4(S)-hydroxy-5-(2-(3(S)-N'-(t-butylcarbamoyl)-(4aS,8aS)-decahydroisoquinoline)yl)-pentaneamide in dioxane is added 6 eq of chloroethyl morpholine and 6 eq of cesium carbonate. The reaction is heated to 90° C. When the reaction is complete, the precipitate is filtered off, the dioxane is concentrated to dryness and the residue is diluted with water which is washed with ethyl acetate. The organic phase is dried, filtered and concentrated to afford the title compound.

EXAMPLE 14

Preparation of N-(2(R)-hydroxy-1(S)-indanyl)-2(R)-((4-(2-(4-morpholinyl)ethoxy)phenyl)methyl)-4(S)-hydroxy-5-(1-(4-carbobenzyloxy-2(S)-N'-(t-butylcarbamoyl)-piperazinyl))pentaneamide To a solution of N-(2(R)-hydroxy-1(S)-indanyl)-2(R)-((4-hydroxyphenyl)methyl)-4(S)-hydroxy-5-(1-(4-carbobenzyloxy-2(S)-(t-butylcarbamoyl)-piperazinyl)-pentaneamide in dioxane is added 6 eq of chloroethyl morpholine and 6 eq of cesium carbonate. The reaction is heated to 90° C. When the reaction is complete, the precipitate is filtered off, the dioxane is concentrated to dryness and the residue is diluted with water which is washed with ethyl acetate. The organic phase is dried, filtered and concentrated to afford the title compound.

EXAMPLE 15

Preparation of N-(2(R)-hydroxy-1(S)-indanyl)-2(R)-phenylmethyl-4(S)-hydroxy-5-(1-(4-(3-pyridylmethyl)-2(S)-N'-(t-butylcarbamoyl)piperazinyl))pentaneamide Step 1
Preparation of dihydro-5(S)-((trifluoromethanesulfonyl)oxymethyl)-3(R)-phenylmethyl-3(2H)-furanone To a solution of 18.4 g (89.2 mmol) of dihydro-5(S)-(hydroxymethyl)-3(R)-phenylmethyl-3(2H)-furanone in 350 mL of methylene chloride cooled to 0° C. was added 13.51 mL 2,6-lutidine (115.98 mmol) followed by a dropwise addition of 16.51 mL of trifluoromethanesulfonic anhydride (98.1 mmol). After 1.5 hours at 0° C., the reaction was poured into a mixture of 300 mL ice/brine and stirred for 0.5 hours. The aqueous layer was then extracted with methylene chloride (3×150 mL), the organic layers were washed with 10% HCl (2×75 mL), saturated NaHCO₃ (100 mL), water (100 mL), dried over MgSO₄, filtered and concentrated to give a solid residue. Purification via flash column chromatography (120×150 mm column, gradient elution of hexanes:EtOAc, 4:1 to 3:1) afforded the title product; mp 53°–54° C.

Step 2
Preparation of 4-(1,1-dimethylethyl)-1-(phenylmethyl)-1,2(S),4-piperazinetricarboxylate The title compound was prepared following the procedure of Bigge, C. F.; Hays, S. J.; Novak, P. M.; Drummond, J. T.; Johnson, G.; Bobovski, T. P. *Tetrahedron Lett.* 1989, 30, 5193; starting with 2(S)-piperazine-carboxylic acid. (see Felder, E.; Maffei, S.; Pietra, S.; Pitre, D.; *Helv. Chim. Acta* 1960, 117,888.

Step 3
Preparation of N-t-butyl-4-(1,1-dimethylethoxycarbonylamino)-1-(phenylmethylcarbonylamino)piperazine-2(S)-carboxamide To 9.90 g (27.16 mmol) of 4-(1,1-dimethylethyl)-1-(phenylmethyl)-1,2(S),4-piperazinetricarboxylate dissolved in 75 mL of DMF and cooled to 0° C. was added 5.73 g (29.88 mmol) of EDC, 4.03 g (29.88 mmol) of HOBt, 3.14 mL (29.88 mmol) of t-butylamine, and finally 4.16 mL (29.88 mmol) of triethylamine. The reaction mixture was stirred for 18 hours and the reaction volume was concentrated by half. The mixture was then diluted with 600 mL of EtOAc and washed with 10% HCl (2×75 mL), saturated NaHCO₃ (1×75 mL), water (3×75 mL) and brine (1×50 mL), dried over MgSO₄ and concentrated to a solid. This solid was triturated with EtOAc: hexane (1:2) and filtered to provide the title product as a white solid; mp 134°–135° C.

Step 4
Preparation of N-t-butyl-4-(1,1-dimethylethoxycarbonylamino)piperazine-2(S-carboxamide To 1.20 g (2.86 mmol) of N-t-butyl-4-(1,1-dimethylethoxy-carbonylamino)-1-(phenylmethylcarbonylamino)piperazine-2(S)-carboxamide and 1.1 g (0.086 mmol) of 10% Pd/C was added 15 mL of methanol. The vessel was charged with hydrogen and the reaction stirred for 2 hours, filtered through celite and washed with ethanol. The solvents were removed in vacuo to provide the title product as a foam.

¹H NMR (300 MHz, CDCl₃) δ6.65 (br, 1H), 4.10 (m, 1H), 3.81 (br, 1H), 3.21 (dd, J=18 and 7 Hz, 1H), 3.02–2.70 (m, 4H), 2.10–2.0 (br, 1H), 1.50 (s, 9H), 1.41(s, 9H).

Step 5
Preparation of dihydro-5(S)-(4-(1,1-dimethylethoxycarbonylamino))-2(S)-N-(t-butylcarbamoyl)-piperazinyl)methyl)-3(R)-phenylmethyl-3(2H)-furanone To a solution of 22.40 g (0.0662 mol) dihydro-5(S)-(trifluoromethanesulfonyl)oxymethyl)-3(R)-phenylmethyl-3(2H)-furanone (prep in Step 1) and 18.0 g (0.063 mol) of n-t-butyl-4-(1,1-dimethylethoxycarbonylamino)piperazine-2(S)-carboxamide dissolved in 180 mL of isopropanol was added 11.53 mL (0.0662 mol) of N,N-diisopropylethylamine. After 2.5 hours another 1.2 g of dihydro-5(S)-((trifluoromethanesulfonyl)oxymethyl)-3(R)-phenylmethyl-3(2H)-furanone was added. The reaction was complete by thin layer chromatography (tlc) after 3.5 hours and was concentrated to a thick oil. Trituration with EtOAc:hexanes (1:2, 200 mL) provided a white solid which was filtered and discarded. The oil was purified by flash column chromatography (120×150 mm column, EtOAc:hexanes gradient elution 1:1, 2:1, 3:1 to all EtOAc) to afford the title compound.

¹H NMR (400 MHz, CDCl₃) δ7.34–7.17 (m, 5H), 6.31 (br s, 1H), 4.38 (br m, 1H), 3.96–3.92 (m, 1H), 3.79 (br m, 1H), 3.16 (dd, J=13.6 and 4.4 Hz, 1H), 3.08–2.99 (m, 3H), 2.90–2.82 (m, 1H), 2.80 (dd, J=13.5 and 8.9 Hz, 1H), 2.78 (m, 1H), 2.67–2.61 (m, 1H), 2.58–2.49 (m, 1H), 2.38–2.32 (m, 1H), 2.32–2.04 (m, 1H), 1.99–1.92 (m, 1H,) 1.45 (s, 9H), 1.29 (s, 9H).

Step 6
Preparation of 2(R)-phenylmethyl-4(S)-(t-butyldimethylsilyloxy)-5-(1-(4-(1,1-dimethylethoxycarbonylamino)))-2(S)-N-(t-butylcarbamoyl)-piperazinyl))pentaneamide To 25.50 g (52.50 mmol) of dihydro-5(S)-(4-(1,1-dimethylethoxycarbonylamino))-2(S)-N-(t-butylcarbamoyl)-piperazinyl)-methyl)-3(R)-phenylmethyl-3(2H)-furanone dissolved in 120 mL DME cooled to 0° C. was added a solution of 60 mL of water and 1.512 g (63.01 mmol) of lithium hydroxide. After 0.5 hours the reaction was quenched with the addition of 10% HCl until pH 6 and the solution was concentrated in vacuo. The residue was dissolved in 50 mL water and extracted with EtOAc (4×75 mL) and the organic layers were washed with water (1×20 mL), brine (1×20 mL). The aqueous was back extracted with EtOAc (2×75 mL) and the combined organic layers were dried over $MgSO_4$ and concentrated to provide a yellow solid. This crude product was dissolved in 100 mL of DMF and 17.87 g (0.262 mol) of imidazole was added, cooled to 0° C. and then 31.50 g (0.21 mol) of t-butyldimethylsilyl chloride was added. This stirred 1 hour at 0° C. and was then warmed to room temperature. After 20 hours the reaction was quenched with 10 mL methanol and concentrated to half the volume. 100 mL of pH 7 buffered water was added and the aqueous was extracted with EtOAc (4×100 mL), the combined organic layers were washed with 10% HCl (2×50 mL), water (3×75 mL), and brine (1×50 mL), dried over $MgSO_4$ and concentrated to obtain the title compound. This material was used directly in the next step.

Step 7

Preparation of N-(2(R)-hydroxy-1(S)-indanyl)-2(R)-phenylmethyl-4(S)-(t-butyldimethylsilyloxy)-5-(1-(4-(1,1-dimethylethoxycarbonylamino)))-2(S)-N-(t-butylcarbamoyl)-piperazinyl))pentaneamide To 27.0 g (0.0446 mol) of the crude material from Step 6 dissolved in 180 mL of DMF and cooled to 0° C. was added 8.98 g (0.0468 mol) of EDC, 6.32 g (0.0468 mol) of HOBt, and 7.31 g (0.049 mol) aminohydroxy indane. Triethylamine (6.52 mL, 0.0468 mol) was added and the reaction stirred at 0° C. for 2 hours, room temperature for 16 hours and was quenched by diluting with 500 mL of EtOAc. The organic layer was washed with 10% HCl (2×100 mL), saturated $NaHCO_3$ (1×100 mL), water (3×150 mL), brine (1×75 mL), dried over $MgSO_4$ and concentrated to yield the title compound as a white foam.

$^1$H NMR (400 MHz, $CDCl_3$) δ7.4–7.17 (m, 9H), 6.51 (br s, 1H), 5.79 (br s, 1H), 5.23 (m, 1H), 4.23 (br s, 1H), 4.06 (m, 1H), 3.96–3.84 (m, 2H), 3.07–2.78 (m, 8H), 3.65 (dd, J=9.6 and 4.1 Hz, 1H), 2.56–2.44 (m, 2H), 2.29 (dd, J=12.0 and 4.5 Hz, 1H), 2.17–2.09 (m, 1H), 1.79 (br s, 1H), 1.44 (s, 9H), 1.35 (s, 9H), 1.10 (s, 1H), 0.84 (s, 9H), 0.12 (s, 3H 0.08 (s, 3H).

Step 8

Preparation of N-(2(R)-hydroxy-1(S)-indanyl)-2(R)-phenylmethyl-4(S)-(hydroxy)-5-(1-(4-(1,1-dimethylethoxycarbonylamino)))-2(S)-N-(t-butylcarbamoyl)piperazinyl))pentaneamide To 32.20 g (0.0437 mol) of N-(2(R)-hydroxy-1-(S)-indanyl)-2(R)-phenylmethyl-4(S)-(t-butyldimethylsilyloxy)-5-(1-(4-(1,1-dimethylethoxycarbonylamino)))-2(S)-N-(t-butylcarbamoyl)piperazinyl))-pentaneamide was added 437 mL (0.437 mol) of tetrabutylammonium fluoride (1.0M solution in THF, Aldrich). The reaction stirred for 18 hours and was then concentrated to 200 mL and diluted with 700 mL of EtOAc. This was washed with water (2×100 mL), brine (1×50 mL) and the aqueous layers were back extracted with EtOAc (2×200 mL). The combined organic layers were dried over $MgSO_4$ and concentrated to an oil. Purification via flash column chromatography (120×150 mm column, gradient elution $CH_2Cl_2$: $CHCl_3$/saturated with $NH_3$: methanol, increasing methanol from 1%, 1.5%, 2%) afforded the title compound as a white foam.

$^1$H NMR (400 MHz, $CDCl_3$) 7.31–7.11 (m, 9H), 6.41 (br s, 1H), 6.23 (d, J=8.6 Hz, 1H), 5.25 (dd, J=8.6 and 4.7 Hz, 1H), 4.21 (m, 1H), 3.83–3.82 (m, 2H), 3.78–3.61 (m, 2H), 3.22–3.19 (m, 2H), 3.03–2.78 (m, 8H), 2.62–2.58 (m, 1H), 2.41–2.35 (m, 2H), 2.04–2.02 (m, 1H), 1.57–1.50 (m, 1H), 1.45 (s, 9H), 1.32 (s, 9H).

Step 9

Preparation of N-(2(R)-hydroxy-1(S)-indanyl)-2(R)-phenylmethyl-4(S)-(hydroxy)-5-(1-(2(S)-N-(t-butylcarbamoyl)-piperazinyl)pentaneamide To 21.15 g (0.034 mol) of N-(2(R)-hydroxy-1(S)-indanyl)-2(R)-phenylmethyl-4(S)-(hydroxy)-5-(1-(4-(1,1-dimethylethoxycarbonylamino)))-2(S)-N-(t-butylcarbamoyl)-piperazinyl))-pentaneamide dissolved in 350 mL of methylene chloride and cooled to 0° C. was added 22.43 mL (0.204 mol) 2,6-lutidine and then 32.85 mL (0.170 tool) of trimethylsilyltriflate over 5 minutes. After 0.5 hours the reaction was quenched with 10% HCl (80 mL) and this stirred 0.5 hours. To this was added 100 mL of saturated $NaHCO_3$ and then solid $NaHCO_3$ until pH 8. The aqueous layer was then extracted with EtOAc (4×100 mL) and the combined organic layers were washed with water (1×50 mL), brine (1×75 mL), dried over $MgSO_4$ and concentrated. The residue was purified via column chromatography (120× 150 mm column, gradient elution $CH_2Cl_2$:$CHCl_3$ saturated with $NH_3$: MeOH, slowly increasing methanol 2%, 3%, 4%, 5%, 6%, to 10%). This provided the title product as a white foam.

$^1$H NMR (400 MHz, $CDCl_3$) δ7.53 (s, 1H), 7.29–7.09 (m, 9H), 6.52 (d, J=8.3 Hz, 1H), 5.24 (dd, J=8.2 and 4.9 Hz, 1H), 4.23 (dd, J=4.7 and 4.03 Hz, 1H), 4.25–4.00 (br s, 1H), 3.83–3.81 (m, 1H), 3.03–2.88 (m, 4H), 2.82–2.73 (m, 7H), 2.50–1.60 (br s, 2H), 2.45 (d, J=6.2 Hz, 2H), 2.32–2.29 (m, 1H), 1.98 (m, 1H), 1.51 (m, 1H), 1.33 (s, 9H).

Step 10

Preparation of N-(2(R)-hydroxy-1(S)-indanyl)-2(R)-phenylmethyl-4(S)-hydroxy-5-(1-(4-(3-pyridylmethyl)-2(S)-N'-(t-butylcarbamoyl)-piperazinyl))pentaneamide To 10.0 g (0.019 mol) of N-(2(R)-hydroxy-1(S)-indanyl)-2(R)-phenylmethyl-4(S)-hydroxy-5-(1(-2(S)-N-(t-butylcarbamoyl)-piperazinyl)-pentaneamide and 3.45 g (0.021 mol) of 3-picolyl chloride dissolved in 40 mL of DMF was added 5.85 mL (0.042 mol) of triethylamine. After 3 hours an additional 0.313 g of 3-picolyl chloride was added. After an additional 2 hours the reaction was diluted with 400 mL of EtOAc and washed with water (3×75 mL), brine (1×100 mL), dried over $MgSO_4$ and concentrated. The residue was triturated with 30 mL of EtOAc and the resulting white precipitate was collected. Further recrystallization from EtOAc provided the title product (mp 167.5°–168° C.).

EXAMPLE 16

Employing substantially the same procedure as described in Example 15, but treating the N-(2(R)-hydroxy-1(S)-indanyl)-2(R)-phenylmethyl-4(S)-hydroxy-5-(1-(2(S)-N'-(t-butylcarbamoyl)-piperazinyl))-pentaneamide used therein (compound (i) below) with the alkylating agent (ii) indicated below in place of the 3-picolyl chloride used in Step 10 therein, the following products defined by formula (iii) were made:

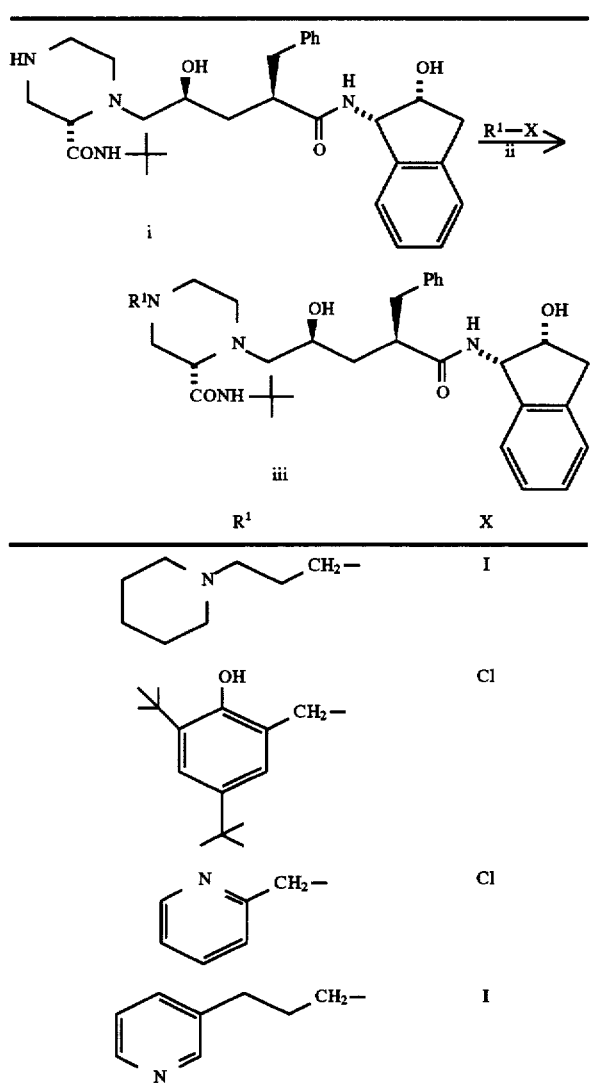

EXAMPLE 17

Preparation of dihydro-5(S)-(tert-butyldimethylsilyloxymethyl)-3(2H)-furanone

To a solution of 3.00 g (25.8 mmol) of dihydro-5(S)-(hydroxymethyl)-2(3H)-furanone dissolved in 25 mL of dichloromethane was added 3.51 g (51.6 mmol) of imidazole and then 4.67 g (31.0 mmol) of tert-butyldimethylsilyl chloride. The reaction stirred at room temperature for 8 hours and was quenched with 2 mL of methanol. The mixture was concentrated to an oil and then diluted with 150 mL of ether and washed with 5% HCl (2×10 mL), saturated NaHCO$_3$ (1×10 mL), water (1×10 mL), and brine (1×10 mL), dried over MgSO$_4$ and concentrated. The residue was purified by flash chromatography (40×150 mm column, gradient elution, hexanes:ethyl/acetate 5:1 to 4:1) to afford the product as a clear oil.

$^1$H NMR (300 MHz, CDCl$_3$) δ4.68–4.60 (m, 1H), 3.89 (dd, J=3.3 and 11.3 Hz, 1H), 3.71 (dd, J=3.2 and 5411.3 Hz, 1H), 2.71–2.45 (m, 2H), 2.35–2.16 (m, 2H), 0.91 (s, 9H), 0.10 (s, 3H), 0.09 (s, 3H).

EXAMPLE 18

Preparation of N-(2(R)-hydroxy-1(S)-indanyl)-2(R)-phenylmethyl-4(S)-hydroxy-5-(1-(4-(4-bromo-2-thiophenemethyl)-2(S)-N'-(t-butylcarbamoyl)-piperazinyl)) pentaneamide

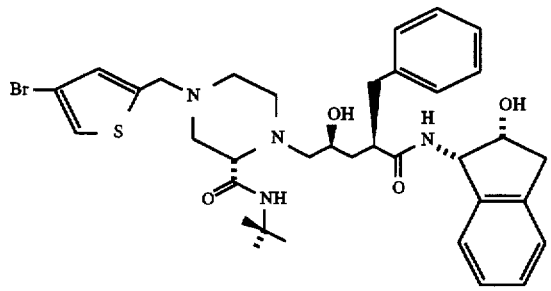

To a solution of 50 mg (0.096 mmol) of N-(2(R)-hydroxy-1(S)-indanyl)-2(R)-phenylmethyl-4(S)-hydroxy-5-(1-(2-(S)-N'-(t-butyl carbamoyl)-piperazinyl)) pentaneamide of Step 9, Example 15, dissolved in 0.4 mL of methanol was added 27.5 mg (0.144 mmol) of 4-bromo-2-thiophene carboxylic aldehyde, 9.0 mg (0.144 mmol) sodium cyanoborohydride and then acetic acid (20 μL) until pH=6. The reaction stirred at room temperature for 8 h and was quenched with 0.5 mL of 1N HCl. The mixture was concentrated to a white solid and then diluted with 50 mL of ethyl acetate and washed with saturated NaHCO$_3$ (1×5 mL), water (1×5 mL), and brine (1×5 mL), dried over MgSO$_4$ and concentrated. The residue was purified by flash column chromatography (15× 150 mm column, gradient elution in methylene chloride: chloroform saturated with NH$_3$:methanol 69:30:1 to 67:30:3 to afford 40.3 mg (60% yield) of the product as a clear oil. An analytical sample was obtained by titration with ethyl acetate and hexanes. Anal. Calcd for C$_{35}$H$_{45}$N$_4$O$_4$BrS 0.4 mol H$_2$O: C, 59.63; H, 6.55; N, 7.95. Found: C, 59.66; H, 6.45, N, 7.86.

EXAMPLE 19

By substantially the same procedure as described in Example 18, but substituting a different aldehyde (R,CHO), the following compounds are prepared.

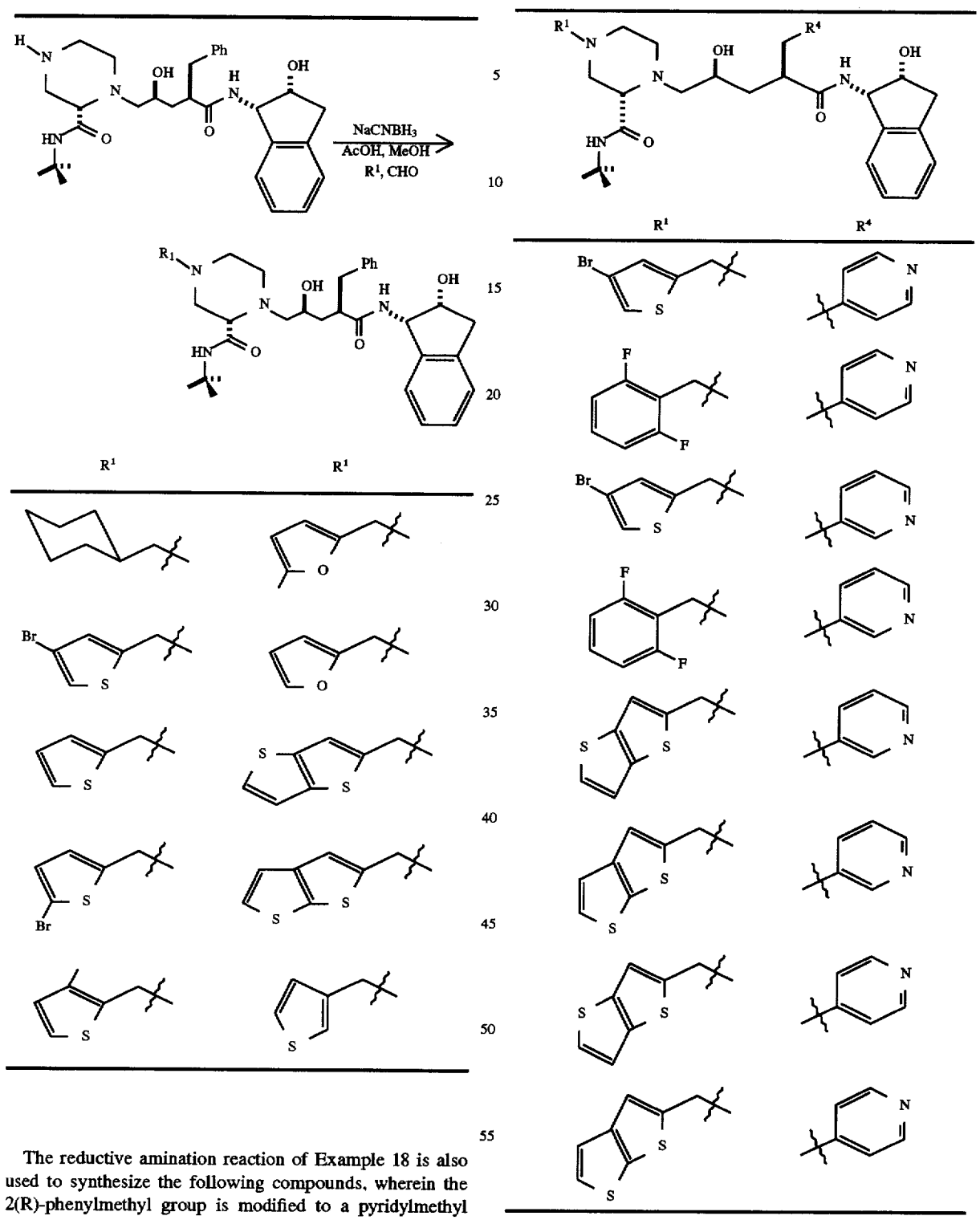
The reductive amination reaction of Example 18 is also used to synthesize the following compounds, wherein the 2(R)-phenylmethyl group is modified to a pyridylmethyl group.

While the foregoing specification teaches the principles of the present invention, with examples provided for the purpose of illustration, it will be understood that the practice of the invention emcompasses all of the usual variations, adaptations, or modifications, as come within the scope of the following claims and its equivalents.

What is claimed is:

1. A process for making a compound of the formula I

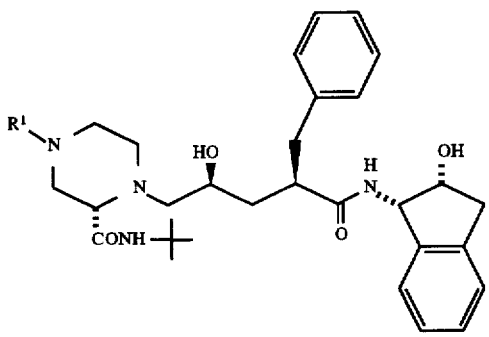

comprising reacting a compound (i) of the formula

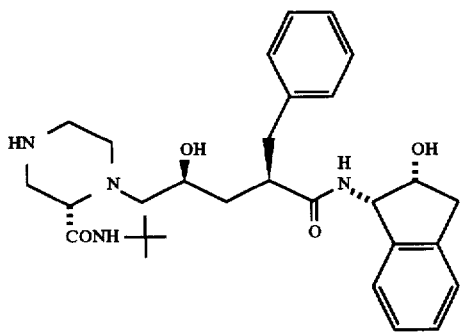

with R$^1$—X; wherein R$^1$ is C$_{1-4}$ alkyl unsubstituted or substituted with one or more of (1) aryl unsubstituted or substituted with one or more of C$_{1-4}$ alkyl, amino, hydroxy or aryl;

(2) a 5–7 membered cycloalkyl group unsubstituted or substituted with one or more of halo, C1–3 alkoxy or aryl; or (3) heterocycle unsubstituted or substituted with one or more of oxo, halo, C$_{1-4}$ alkoxy, C$_{1-4}$ alkyl, —C(O)OC$_{1-3}$ alkyl, —NHC(O)C$_{1-3}$ alkyl, or Boc; and X is selected from Cl, Br or I;

to give the compound of formula I.

2. The process of claim 1, wherein

R$^1$ is C$_{1-4}$ alkyl unsubstituted or substituted with a heterocycle wherein the heterocycle is unsubstituted or substituted with one or more of oxo, halo, C$_{1-4}$ alkoxy, C$_{1-4}$ alkyl, —C(O)OC$_{1-3}$ alkyl, —NHC(O)C$_{1-3}$ alkyl, or Boc.

3. The process of claim 2, wherein

R$^1$ is C$_{1-4}$ alkyl substituted with a heterocycle, wherein the heterocycle is selected from piperidinyl, pyridyl, thienyl, pyrrolyl, thiazolyl, imidazolyl, furyl, benzimidazolyl, pyrazinyl, isoxazolyl, pyridazinyl, or quinolinyl, and wherein the heterocycle is unsubstituted or substituted with one or more of oxo, halo, C$_{1-4}$ alkoxy, C$_{1-4}$ alkyl, —C(O)OC$_{1-3}$ alkyl, —NHC(O)C$_{1-3}$ alkyl, or Boc.

4. The process of claim 3 for making a compound J of the formula

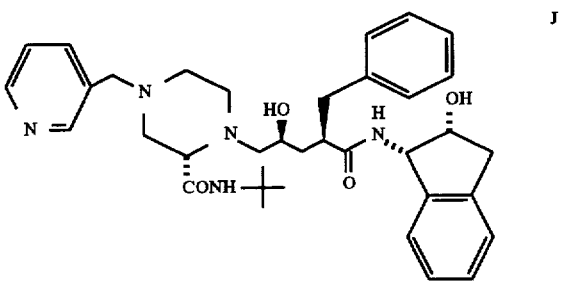

comprising reacting a compound (i) of the formula

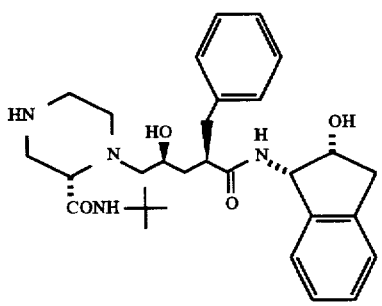

with a compound of the formula

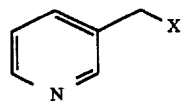

to give the compound J.

5. The process of claim 4 for making a compound J of the formula

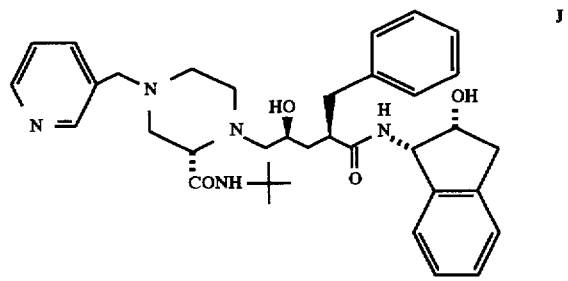

comprising reacting a compound (i) of the formula

81
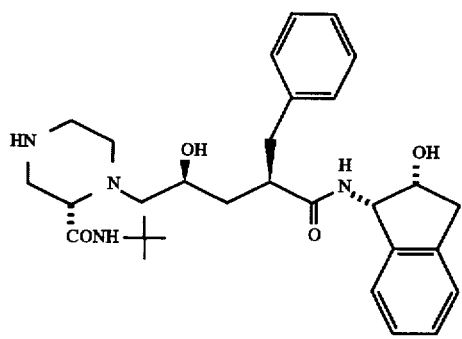
with 3-picolyl chloride to give the compound J.
6. A compound (i) of the formula:
82
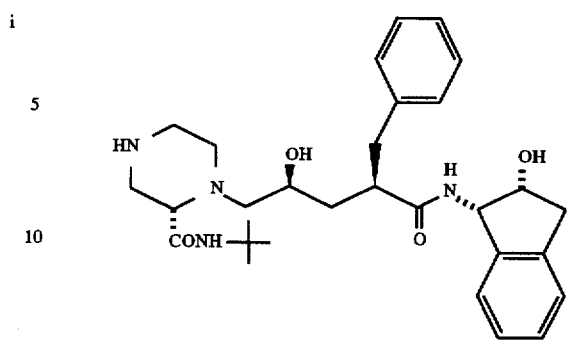
or a salt thereof.
* * * * *